(12) United States Patent
Peltz et al.

(10) Patent No.: US 6,630,294 B1
(45) Date of Patent: Oct. 7, 2003

(54) SUBFAMILY OF RNA HELICASES WHICH ARE MODULATORS OF THE FIDELITY OF TRANSLATION TERMINATION AND USES THEREOF

(75) Inventors: Stuart Peltz, Piscataway, NJ (US); Kevin Czaplinski, Somerset, NJ (US); Jonathan D. Dinman, North Brunswick, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 09/359,268

(22) Filed: Jul. 22, 1999

Related U.S. Application Data

(60) Provisional application No. 60/093,685, filed on Jul. 22, 1998.

(51) Int. Cl.⁷ .............................. C12Q 1/00; C12N 9/00; G01N 33/53; G01N 33/00; C07K 17/00
(52) U.S. Cl. .............................. 435/4; 435/183; 435/71; 530/350; 436/86; 536/23.2
(58) Field of Search .............................. 435/4, 7.1, 183; 530/350; 536/23.2; 436/86

(56) References Cited

U.S. PATENT DOCUMENTS

| | | |
|---|---|---|
| 5,641,627 A | 6/1997 | Moehle et al. ............... 435/6 |
| 5,679,566 A | 10/1997 | He et al. .................... 435/325 |
| 5,840,702 A | 11/1998 | Bedwell et al. ............. 514/23 |
| 5,874,231 A | 2/1999 | Sonenberg et al. ......... 435/7.21 |
| 5,994,119 A | 11/1999 | Dietz ........................ 435/254.21 |

FOREIGN PATENT DOCUMENTS

| | | |
|---|---|---|
| WO | WO 97/12617 | 4/1997 |
| WO | WO 97/34611 | 9/1997 |
| WO | WO 97/40855 | 11/1997 |

OTHER PUBLICATIONS

Broun et al., Science 282:1315–1317, 1998.*
Van de Loo et al., Proc. Natl. Acad. Sci. 92:6743–6747, 1995.*
Bork, Genome Research, 10:398–400, 2000.*
Biswas, E. et al., Biochem. Biophys. Res. Commun., vol. 206, No. 3, pp. 850–856, Jan. 1995.*
Branch TIBS 23:45–50 (Feb. 1998).
Czaplinski, et al. RNA 1:610–623 (1995).
Czaplinski, et al. Bioessays 21:685–696 (1999).
Czaplinski, et al. Genes & Development 12:1665–1677 (Jun. 1998).
Andjelkovic, et al. Medline Abstract 2191 (EMBOJ. 15:7156–7167 (1996).
Peltz, et al. Progress in Nucleic Acid Research and Molecular Biology 47:271–298 (1994).
Weng, et al. Molecular and Cellular Biology 16:5477 (1996).
Frovola, et al., RNA 2:334–341. (1996).
Howard, et al., Nature Medicine 2:467–469 (1996).

* cited by examiner

Primary Examiner—Rebecca E. Prouty
Assistant Examiner—Delia Ramirez
(74) Attorney, Agent, or Firm—Michael J. Wise; Perkins Coie LLP

(57) ABSTRACT

This invention provides a method for modulating the efficiency of translation termination of messenger RNA. Also provided are methods of screening for compositions and agents capable of modulating translation termination.

4 Claims, 6 Drawing Sheets

FIG. 1A-1

```
Mttl      793  ..............................SQIFTNIAAGGREIKVIK.E.......CP
Upfl      547  ..............................ADVVCCTCVGAGDKRIDT...K......FR
Senl     1413  DRDEMREKNSVNYRNRDLDRRNAQAHILAVSDIICSTLSGSAHDVIATMGIK........FD
Dipl      351  ..............................FKTIKDLIIQSRIVTTLHGSSSRELCSLYRDDPNFQIFD
Dna2     1128  KHKVHPDTQKYVPNYASVKSYNDYLSKINSTSVAATTCIGI.NDIIFTINEKD.......FD
consensus 241  ............................l s iv tT igg rL ti k         fd Mttl      816  VVIMDEATQSSEASTIVPISLPGIR..NFVFVGDEKQISSFSNIP................QLE
Upfl      568  TVIIDESTQASEPECLIPI..VKGAK..QVILVGDHQQIG..PVILERKAADA..GLK
Senl     1467  TVIIDEACQCTELSSIIPIRY.GGK..RCIMVGDPNQI................PPTVLSGAASNF..KYN
Dipl      391  TIIDEVSQAMEPQCWIPLIAHQNQFHKLVIAGDNKQI................PPTIKTEDDKNVIHNLE
Dna2     1182  YVIIDEASQISMEVAIGPIRY...GNRFIMVGDHYQL................PPIVKNDAPR..LGGLE
consensus 301  tviiDeatQ sep liPl     g  r ilvGD QL                pP i  a        le Mttl      862  TSLFERVLSNGTYKNELM..IDTQYRMHFKISEFFIKKIYNGEI
Upfl      618  QSLFERLLISLGHV..FIR..IEVQYRMNFYLSEFPSNMFYEGSL
Senl     1517  QSLFVRMEKN...SSEYL..LDVQYRMHPSISRFPSSEFYQGRL
Dipl      446  TLFDRIIKIFPKRDMVKFLNVQYRMNQRIMEFPSHSMYNGKLLADATVANRLLIDLPTV
Dna2     1231  ESLFKTFCEKHPES..VAEITLQYRMCGDIVTLSNFLIYDNKLKCGNNEVFAQSLELPMP
consensus 361  sLFervl              pl   LdvQYRM p isefps  iYngrL Mttl      904  ..............................................
Upfl      658  ..............................................
Senl     1556  ..............................................
Dipl      506  DA...............................................
Dna2     1289  EALSRYRNESANSKQWLEDILEPTRKVFLNYDNCPDIIEQSERDNITNHGEAELTLQCV
consensus 421  ..............................................
```

FIG. 1B

```
Mtt1       904 .........KDGVTDEQKA.........WFGVQH.................PLFFYQCDLGFESR
Upf1       658 .........QNGVTIEQRTVPNSKFPWEIRGI.................PMMFW.ANYGRE.
Sen1      1556 .........KDG.................PGMDILNKRPWHQLEPLAPYKEFDIISGRQ..
Dip1       508 .........TPSED...................................DDDTKIELIWYD.TQGDEFQ
Dna2      1349 EGMLLSGVPCED..................................................
consensus  481              dg                p              pl fy  g  e Mtt1       934 VRSTQRDIVGFTYE.........NKHECVEIVKIIQIIMLDKKVPLE...EI
Upf1       692 .....EISANGTSFL.........NRIEAMNCERIITKLFRDGVKP.E..QI
Sen1      1589 .....EQNAKTMSYT.........NMEEIRVAIELVDYIFRKFDNKIDFTGKI
Dip1       532 ETADEATILGSKYNEGEIAIVKEHIENLRSENVFE...................NSI
Dna2      1361 ..............................................................
consensus  541        e     g  ty             n   e             ii  l      e       I Mtt1       974 GVITPYSAQRDLISDILTKNVVINPKQISMQQEYDEIELFNAAGSQTAGSLQNNVINII...
Upf1       727 GVITPYEGQRAYILQYMQMN..........................GSLDK...DLY
Sen1      1628 GIISPYREQ.....................................MQKMRKEFARYFGMINKS
Dip1       570 GVISPYNAQVSHIRKLIHDELKLTD......................................
Dna2      1362 GVMTHMRAQLRILRKIFNKNV..........................................
consensus  601 GvitpY aQ    l  il  nv                              g l Mtt1      1034 NGLHVATVDSFQGMEKSFIIFSCVRN.NTENKIGFLRDKRFLNVALTRAK~
Upf1       755 IKVEVASVDAFQGREKDYIILISCVRA.NEQQAIGFLRDERRLNVGLTRAK~
Sen1      1656 ..IDFNTIDGFQGQEKEIDLISCVRADDTKSSVGFLKDFRFMNVALTRAK~
Dip1       595 ..IEISTVDGFQGREKDVIITLSTVRS.NEKFEVGFLKEERRLNVAMTRPR~
Dna2      1384 DGLEILTRDQFQGRDNKCIIISMVFRNSQLNGGAILKELRFVNVAMTRAKS
consensus  661    lev  tvdaFQGreKd Iil ScVR  n   n igfLkd RRlNValTRak
```

SUBFAMILY OF RNA HELICASES WHICH ARE MODULATORS OF THE FIDELITY OF TRANSLATION TERMINATION AND USES THEREOF

DOMESTIC PRIORITY CLAIMED

The priority is claimed of U.S. Provisional Application No. 60/093,685, filed on Jul. 22, 1998, which is hereby incorporated by reference herein in its entirety.

GOVERNMENT RIGHTS CLAUSE

The research leading to the present invention was supported, at least in part, by a grant from The National Institutes of Health (GM48631-01). Accordingly, the Government may have certain rights in the invention.

FIELD OF THE INVENTION

The present invention relates to a subfamily of RNA helicases, one of which is the MTT1 gene, which modulates the fidelity of translation termination. The present invention relates to a multiprotein surveillance complex comprising MTT1, human Upf1p, Upf2p, Upf3p, eucaryotic Release Factor 1 and eucaryotic Release Factor 3 which is involved in modulation of the efficiency of translation termination and degradation of aberrant mRNA. Identification of this complex provides an in vitro assay system for identifying agents that: affect the functional activity of mRNAs by altering frameshift frequency; permit monitoring of a termination event; promote degradation of aberrant transcripts; provide modulators (inhibitors/stimulators) of peptidyl transferase activity during initiation, elongation, termination and mRNA degradation of translation. Such agents which may be antagonists or agonists, are useful for screening, and diagnostic purposes, and as therapeutics for diseases or conditions which are a result of, or cause, premature translation.

BACKGROUND OF THE INVENTION

The translational apparatus is responsible for synthesizing cellular proteins. This machinery must be able to determine the precise sites on the mRNA where decoding should begin and where it should end. The selection of the translation start site is usually delineated by the first AUG codon encoding the amino acid methionine. After initiation of translation, the ribosome manufactures the polypeptide by progressing along the mRNA in the 5' to 3' direction, decoding one codon at a time. The final step in the translation process occurs when one of three termination codons occupies the A-site of the ribosome, resulting in hydrolysis of the peptide (reviewed in Buckingham et al., 1997). Although translation termination normally occurs after completion of the full-length polypeptide, base substitutions and frameshift mutations in DNA often lead to the synthesis of an mRNA that contains an inappropriate stop codon within its protein coding region. The occurrence of such a premature stop codon arrests translation at the site of early termination and causes the synthesis of a truncated protein and rapid degradation of the mRNA (reviewed in Ruiz-Echevarria et al., 1996; Weng et al., 1997). Interestingly, nonsense and frameshift mutations cause approximately 20–40% of the individual cases of over 240 different inherited diseases (reviewed in McKusick, 1994). Thus, treatment of a number of genetic disorders can be envisioned by promoting nonsense suppression. Nonsense suppression results when a near cognate tRNA successfully competes with the termination factors at a nonsense mutation so that amino acid incorporation into the peptide chain occurs rather than prematurely terminating translation (FIG. 1). Sufficient levels of nonsense suppression allows production of completed polypeptide protein. For many diseases in which only one percent of the functional protein is produced, patients suffer serious disease symptoms, whereas boosting expression to only five percent of normal levels can greatly reduce the severity or eliminate the disease (McKusick, 1994; Cooper etc.). Recent reports have demonstrated that sub-inhibitory concentrations of certain aminoglycosides suppress the translation termination process, resulting in the expression of full-length CFTR and restoring cyclic AMP-activated chloride channel activity (Bedwell et al. 1997; Howard et al., 1996). Thus, identifying and characterizing the factors that regulate the efficiency of the translation termination will be important for understanding the biology of this process as well as in developing therapeutics for the treatment of a wide array of genetic disorders that arise as a consequence of a nonsense mutations.

Translation termination is carried out by the eucaryotic peptidyl release factors Release Factor 1 (eRF1) and Release Factor 3 (eRF3). Both eRF1 and eRF3 are conserved proteins that interact and promote peptidyl release in eucaryotic cells (Frolova et al. 1994, Stansfield et al. 1995, Zhouravleva et al. 1995). In yeast, eRF1 and eRF3 are encoded by the SUP45 and SUP35 genes, respectively (Frolova et al. 1994, Zhouravleva et al. 1995). Sup45p (eRF1) and Sup35p (eRF3) have been shown to interact (Stansfield et al. 1995, Paushkin et al 1997a,b). eRF1 contains intrinsic peptide hydrolysis activity while eRF3, which has homology to the translation elongation factor EF1$\alpha$ (Didichenko et al. 1991), demonstrates GTPase activity (Frolova et al. 1996), and enhances the termination activity of eRF1 in a GTP-dependent manner (Zhouravleva et al. 1995).

Factors that modulate the efficiency of translation termination process have been identified (Weng et al., 1996a,b; Czaplinski et al., 1998; Song and Liebman, 1987; All-Robyn et al. 1990). For example, recent results indicate that the Upf1p is a factor that modulates the efficiency of translation termination. Disruption of the UPF1 gene results in a dramatic stabilization of nonsense-containing mRNAs and promotes suppression of certain nonsense alleles (Leeds et al. 1991, Cui et al. 1995, Czaplinski et al. 1995,1998 Weng et al. 1996a,1996b). Recent results suggest that the Upf1p may modulate the translation termination process by directly interacting with eRF1 and eRF3 (Czaplinski et al., 1998). The Upf1p contains a cysteine- and histidine-rich region near its amino terminus and all the motifs required to be a member of the superfamily group I helicases (Czaplinski et al. 1995,; Weng et al. 1996a,b, 1998, Altamura et al. 1992, Cui et al. 1996, Koonin, 1992, Leeds et al. 1992, Atkin et al. 1995,1997). The yeast Upf1p has been purified and demonstrates RNA-dependent ATPase and helicase activity (Czaplinski et al. 1995, Weng et al. 1996a,b, 1998). A human homologue of the UPF1 gene, called RENT1 or HUPF1 (Perlick et al. 1996, Applequist et al. 1997) has been identified and shown to be functional in yeast cells in enhancing translation termination, indicating that its role in this process is evolutionarily conserved (Czaplinski et al., 1998).

The results presented here identify a set of superfamily group I helicases in yeast cells with significant homology to Upf1p. In particular, one gene and its protein product called MTT1 (for Modulator of Translation Termination) has been characterized. Mtt1p encodes a superfamily group I helicase and harbors a cysteine-histidine-rich region in its amino terminus. Similar to Upf1p, Mtt1p interacts with the translation termination factor eRF3 and can modulate the translation termination process. Significantly, inactivation of both Upf1p and Mtt1p demonstrate a dramatic nonsense suppression phenotype that is greater than the nonsense suppression phenotype observed for either deletion. These results demonstrate that there is a family of RNA helicases that are modulators of the translation termination process.

SUMMARY OF THE INVENTION

This invention provides a method for identifying a test composition or agent which modulates the efficiency of translation termination which comprises: (a) contacting MTT1 with a test composition under conditions permitting binding between MTT1 and the test composition; (b) detecting specific binding of the test composition to the MTT1; and (c) determining whether the test composition inhibits the MTT1 so as to identify a test composition which is which modulates the efficiency of translation termination. In one embodiment, the agent inhibits ATPase/helicase activity of MTT1, ATPase of Upf1p; GTPase activity of eRF1 or eRF3; RNA binding; binding of the factors to the ribosome; or binding of the factors to each other. In another embodiment the agent modulates the binding of MTT1 to the polysome. In another embodiment the agent inhibits the binding of human MTT1 to eRF3. In another embodiment the agent facilitates the binding of human MTT1 to eRF3.

This invention provides a method of identifying a test composition or agent which modulates binding to MTT1, the method comprising: (a) incubating components comprising the test composition, and MTT1 wherein the incubating is carried out under conditions sufficient to permit the components to interact; and (b) measuring the effect of the test composition on the binding to MTT1. In one embodiment the method further comprising identifying a gene comprising; (a) introducing into a cell a test composition which modulates binding to MTT1; (b) determining the phenotype of the cell after (a); (c) comparing the cellular phenotype after (a) with the cellular phenotype before (a); and (d) identifying the gene of the cell into which the test composition has been introduced.

This invention provides a vector which modulates the expression of MTT1 polynucleotide or the function of MTT1 polypeptide. In one embodiment the modulation is inhibitory. In another embodiment the modulation is stimulatory.

This invention provides an isolated multiprotein complex comprising a MTT1 gene, human Upf1p protein, a peptidyl eucaryotic release factor 1 (eRF1) and a peptidyl eucaryotic release factor 3 (eRF3), wherein the complex is effective to modulate peptidyl transferase activity during translation. In one embodiment the complex further comprising human Upf3p and/or Upf2p.

This invention provides an agent which binds to the complex which modulates the fidelity of translation of an mRNA. Translation includes initiation, elongation, termination as well as degradation. In one embodiment, the agent inhibits ATPase/helicase activity of MTT1, ATPase of Upf1p; GTPase activity of eRF1 or eRF3; RNA binding; binding of the factors to the ribosome; or binding of the factors to each other. In another embodiment the agent modulates the binding of MTT1 to the polysome. In another embodiment the agent inhibits the binding of human MTT1 to eRF3. In another embodiment the agent facilitates the binding of human MTT1 to eRF3.

This invention provides a method of modulating peptidyl transferase activity during translation, comprising contacting a cell with the agent, in an amount effective to suppress nonsense translation termination, thereby modulating the peptidyl transferase activity. The peptidyl transferase activity during translation occurs during initiation, elongation, termination and degradation of mRNA.

This invention provides a method of modulating the efficiency of translation termination of mRNA at a nonsense codon and/or promoting degradation of aberrant transcripts, comprising contacting a cell with the agent, in an amount effective to inhibit the binding of Mtt1 and eRF3, thereby modulating the efficiency of translation termination of mRNA at a nonsense codon and/or promoting degradation of aberrant transcripts.

This invention provides a method of modulating the efficiency of translation termination of mRNA at a nonsense codon and/or promoting degradation of aberrant transcripts, comprising contacting a cell with an agent, which inhibits the ATPase/helicase activity of MTT1, thereby modulating the efficiency of translation termination of mRNA at a nonsense codon and/or promoting degradation of aberrant transcripts.

This invention provides a method of detecting a disorder associated with the expression of Mtt1 protein, wherein the method comprises contacting a sample from a subject having or suspected of having a disorder with a reagent that detects expression of the mtt1 protein or mutant thereof and detecting the binding of the reagent in the sample.

This invention provides a method for treating a disease associated with peptidyl transferase activity, comprising administering to a subject a therapeutically effective amount of a pharmaceutical composition comprising the complex, mtt1 protein, mutant mtt1 protein, or agents thereto, and a pharmaceutical carrier or diluent, thereby treating the subject.

This invention provides a method of identifying genes which are involved in modulation of the fidelity of translation termination, which comprises: a) isolated a gene of interest; and b) determining whether the gene of interest comprises motifs I–IX, wherein if the gene comprises any one of the nine motifs the gene modulates translation termination. In one embodiment motif I comprises the sequence: GppGTKTxT-X(n) (SEQ ID NO:1). In another embodiment motif II comprises the sequence riLxcaSNxAvDxl-X(n) (SEQ ID NO:2). In another embodiment motif III comprises the sequence vviDExxQaxxxxxiPi-X(n) (SEQ ID NO:3). In another embodiment motif IV comprises the sequence xxi1 aGDxxQLp-X(n) (SEQ ID NO:4). In another embodiment motif V comprises the sequence lxx SLF erv-X(n) (SEQ ID NO:5). In another embodiment motif VI comprises the sequence LxxQYRMhpxisefpxYxgxL-X(n) (SEQ ID NO:6). In another embodiment motif VII comprises the sequence IgvitPYxxQvxxl-X(n) (SEQ ID NO:7). In another embodiment motif VIII comprises the sequence vevxtVDxFQGreKdxlilSc VR-X(n) (SEQ ID NO:8). In another embodiment motif IX comprises the sequence iGFLxdxR-RINValTRak.

BRIEF DESCRIPTION OF THE DRAWINGS

FIGS. 1A and 1B. 5 yeast proteins define a subclass of superfamily group I helicases. The MTT1, UPF1, DIP1, SEN1 and DNA2 helicase domains were aligned using PILEUP and the results plotted using BOXSHADE in the GCG program. The consensus sequence is listed on the bottom line. Conserved identical residues (dark gray box) are indicated by capital letters, while conserved similar residues are indicated by lowercase letters (light gray box). Amino acid number within the primary sequence of the respective genes is indicated in the figure. The sequence ID number for MTT1 is SEQ ID NO:25, that for UPF1 is SEQ ID NO:29, that for DIP1 is SEQ ID NO:28, that for SEN1 is SEQ ID NO:26, that for DNA2 is SEQ ID NO:27. The sequence ID numbers for the consensus sequences are as follows: liqGpPGTGKT (SEQ ID NO:12), rivLcapsniavD (SEQ ID NO:13); ikilr (SEQ ID NO:14); kkre (SEQ ID NO:15), fdtviiDeatQ (SEQ ID NO:16), lipl (SEQ ID NO:17), ilvGD (SEQ ID NO:18), SLFervl (SEQ ID NO:19), LdvQYRM (SEQ ID NO:30); isefps (SEQ ID NO:31); iYngrL (SEQ ID NO:32); Gvitpy (SEQ ID NO:20); tvDaFQGreKd (SEQ ID NO:21); IilScVR (SEQ ID NO:22); igfLkd (SEQ ID NO:23); and RRINValTRRak (SEQ ID NO:24).

DETAILED DESCRIPTION OF THE INVENTION

Translation termination at a termination codon is the final step which completes the synthesis of a polypeptide. Premature translation termination leads to the synthesis of truncated proteins and rapid degradation of aberrant mRNAs. These mutations account for a large percentage of inherited genetic disorders and a novel strategy to reduce the efficiency of the translation termination process has been developed for the treatment of these diseases. Thus, the identification and characterization of factors that modulate the termination efficiency will be important for both understanding the biology of this process as well as in identifying new therapeutic agents.

This invention provides on the identification and characterization of a family of RNA helicases involved in modulating translation termination, in particular, the MTT1 gene and its protein product. mtt1Δ strains do not affect mRNA decay but demonstrates a nonsense suppression phenotype. A mtt1Δupf1Δ strain demonstrates a dramatic nonsense suppression phenotype that is greater than observed in strains harboring a single deletion. Biochemical results demonstrate that Mtt1p ATPase/helicase is involved is polysome-associated and interacts with the a translation termination factor eRF3. Taken together, the results presented herein identify a family of RNA helicases that modulate the translation termination efficiency in cells.

The present invention provides a mutant mtt1Δ strain. The present invention provides a mutant mtt1Δ upf1Δ strain which demonstrates a dramatic nonsense suppression phenotype that is greater than observed in strains harboring a single deletion. This invention provides assays, therapeutic agents, and screening methods which act as antagonist or agonist to modulate nonsense suppression. As shown herein, a mtt1Δ upf1Δ strain demonstrates a dramatic nonsense suppression phenotype compared with a mtt1Δ upf1Δ strain.

This invention provides an isolated complex comprising MTT1, a human Upf1p protein, a peptidyl eucaryotic release factor 1 (eRF1) and a peptidyl eucaryotic release factor 3 (eRF3), wherein the complex is effective to modulate peptidyl transferase activity. As defined herein a "surveillance complex" comprises at least MTT1, Upf1p; and eucaryotic Releasing Factor 1 and 3. The "UPF1" gene, is also called RENT1 or HUPF1. The complex may also comprise Upf2p and /or Upf3p.

This invention provides an agent which binds to the complex which modulates the fidelity of translation termination. Translation termination includes initiation, elongation, termination and degradation. In one embodiment the agent modulates the binding of MTT1 to the polysome. In another embodiment the agent inhibits the binding of human MTT1 to eRF3. In another embodiment the agent facilitates the binding of MTT1 to eRF3.

Figure 3:
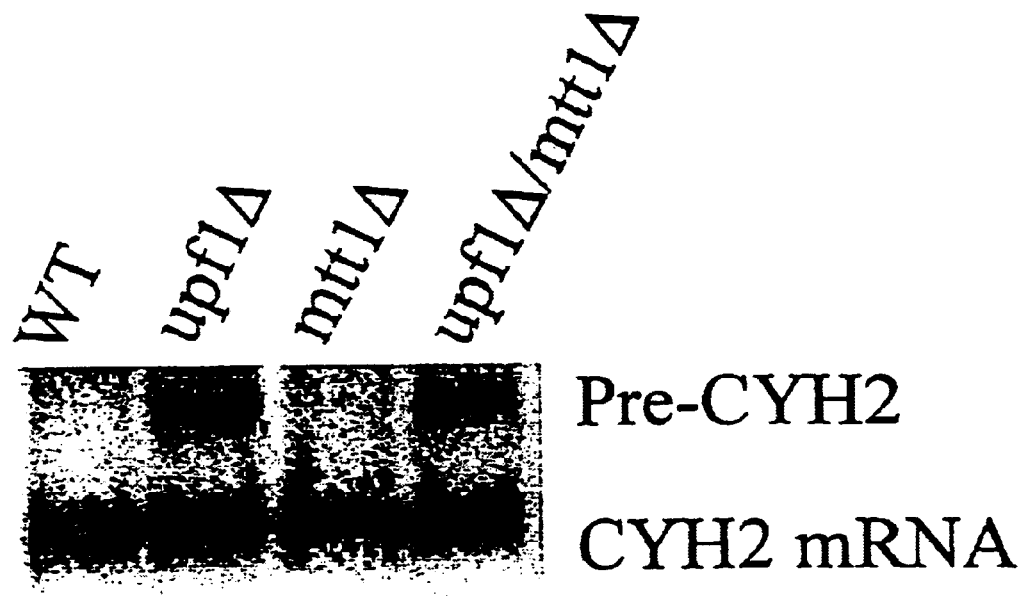
FIG. 3 Mtt1 is not required for nonsense mediated mRNA decay. UPF1, or MTT1 and UPF1 were deleted from yeast strain KC2 (ura3-52 trp1D leu2-2 tyr7-1) and these cells were grown to $OD_{600}$=0.8. Total RNA was prepared and subjected to RNA blotting analysis, using a probe for CYH2 mRNA.
Figure 4:
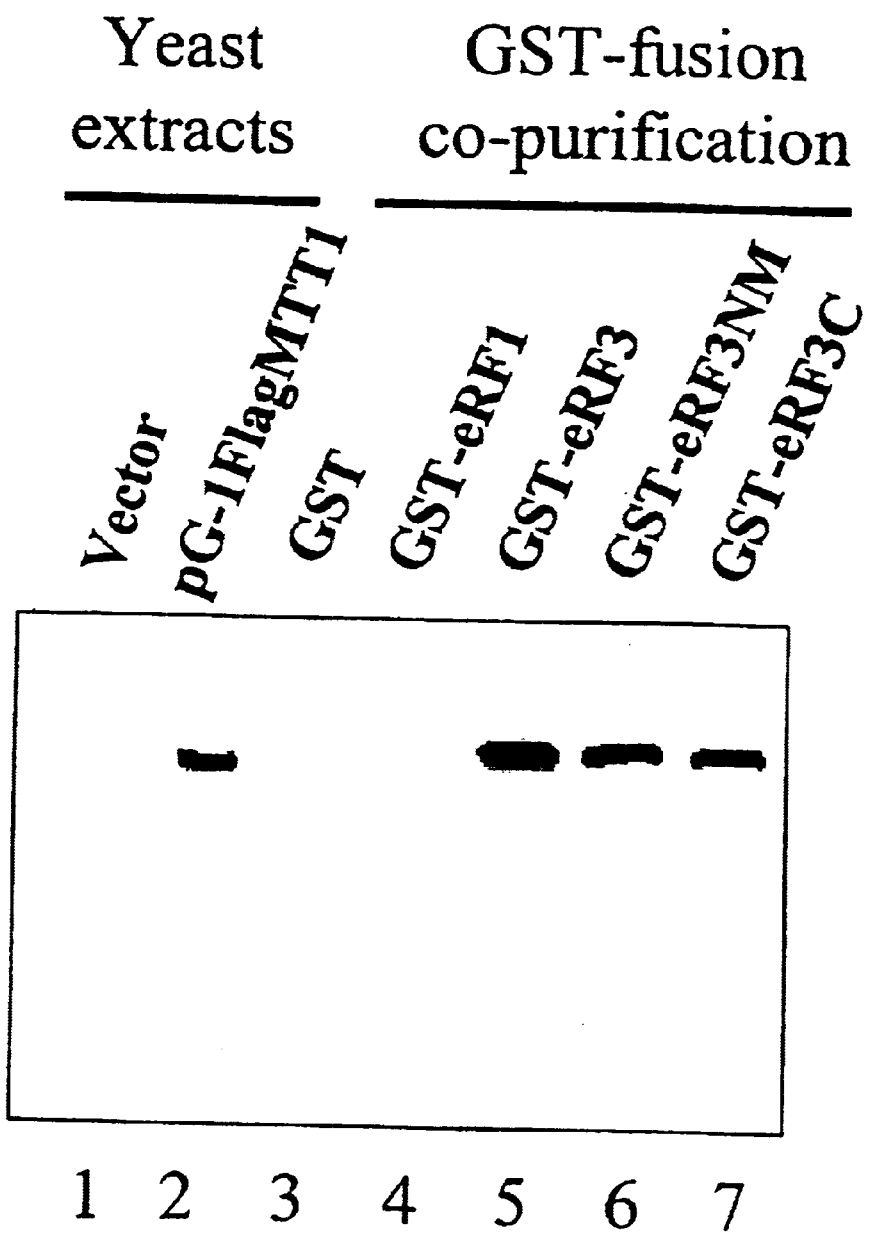
FIG. 4 Mtt1 interacts withe eRF3. Cytoplasmic extracts from a yeast strain BJ3505 transformed with either pG-1 (vector) or pG-1FLAGMTT1 (Flag-Mtt1p) were prepared in IBTB and incubated with 30 μl GST, GST-eRF1, GST-eRF3, GST-eRF3NM or GST-eRF3C sepharose-protein complexes. The sepharose-protein complexes were washed 2 times in IBTB (see materials and methods), resuspended in SDS-PAGE loading buffer, separated on an 8% SDS-PAGE gel and immunoblotted using anti-FLAG antibody.

The results presented here demonstrated that the purified Mtt1p also shows RNA-dependent ATPase and helicase activities (FIG. 7). Several lines of evidence suggest that Mtt1p is involved in translation termination The results presented here show that; 1) a mtt1Δ strain demonstrates a nonsense suppression phenotype (FIG. 4); 2) the Mtt1p is polysome associated (FIG. 6); 3) the Mtt1p directly interacts with the peptidyl release factor eRF3 (FIG. 5); 4) mtt1Δ strains demonstrate paromomycin sensitivity. If one considers that, unlike a upf1Δ strain, a mtt1Δ strain does not stabilize nonsense-containing transcripts, then the amount of nonsense suppression per RNA molecule is greater in a mtt1Δ strain than in a upf1Δ strain (FIG. 3).

A large number of observations point to an important role for protein synthesis in the mRNA decay process. In fact, it appears that these two processes have co-evolved and that factors essential for one process also function in the other. Evidence for this linkage includes experiments demonstrating that: a) drugs or mutations that interfere with translational elongation promote mRNA stabilization, b) sequence elements that dictate rapid mRNA decay can be localized to mRNA coding regions and the activity of such elements depends on their translation, c) degradative factors can be ribosome-associated, and d) premature translational termination can enhance mRNA decay rates.

Since the quantity of a particular protein synthesized in a given time depends on the cellular concentration of its mRNA it follows that the regulation of mRNA decay rates provides a powerful means of controlling gene expression.

In mammalian cells, mRNA decay rates (expressed as half-lives) can be as short as 15–30 minutes or as long as 500 hours. Obviously, such differences in mRNA decay rates can lead to as much as 1000-fold differences in the level of specific proteins. An additional level of control is provided by the observation that decay rates for individual mRNAs need not be fixed, but can be regulated as a consequence of autogenous feedback mechanisms, the presence of specific hormones, a particular stage of differentiation or the cell-cycle, or viral infection.

Perhaps the best examples of the integration of translation and mRNA decay are studies documenting the consequences of premature translational termination. This occurs when deletion, base substitution, or frameshift mutations in DNA lead to the synthesis of an mRNA that contains an inappropriate stop codon (nonsense codon) within its protein coding region. The occurrence of such a premature stop codon arrests translation at the site of early termination and causes the synthesis of a truncated protein. Regardless of their "normal" decay rates, mRNAs transcribed from genes that harbor nonsense mutations (dubbed "nonsense-containing mRNAs"are degraded very rapidly. Such "nonsense-mediated mRNA decay" is ubiquitous, i.e., it has been observed in all organisms tested, and leads to as much as ten-to one hundred-fold reduction in the abundance of specific mRNAs. The combination of severely reduced mRNA abundance and prematurely terminated translation causes reductions in the overall level of expression of specific genes that are as drastic as the consequences of gene deletion. The importance of nonsense-mediated mRNA decay to human health is illustrated by the identification of a growing number of inherited disease in which nonsense mutations cause the disease state and in which nonsense mutations cause the disease state and in which the respective mRNAs have been shown to be substrates of the nonsense-mediated mRNA decay pathway.

An important point is that inactivation of the nonsense-mediated mRNA decay pathway can be accomplished without impeding cellular growth and leads to the restoration of normal levels and normal decay rates for nonsense-containing mRNA's. More significantly, the yeast experiments (and others) demonstrate that, although an mRNA may still contain a nonsense codon, inactivation of this decay pathway allows enough functional protein to be synthesized that cells can overcome the original genetic defect. Thus, it is possible to treat diseases causes by nonsense mutations by downregulating the nonsense-mediated mRNA decay pathway.

This invention provides an expression vector which comprises a nucleic acid encoding a MTT1, Upf1p Upf2p, Upf3p protein, a peptidyl eucaryotic release factor 1 (eRF1) and a peptidyl eucaryotic release factor 3 (eRF3) operably linked to a regulatory element.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control. A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A "nucleic acid molecule" refers to the phosphate ester polymeric form of ribonucleosides (adenosine, guanosine, uridine or cytidine; "RNA molecules"or deoxyribonucleosides (deoxyadenosine, deoxyguanosine, deoxythymidine, or deoxycytidine; "DNA molecules", or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5'direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. A coding sequence is "under the control" of transcriptional and translational control sequences in a cell when RNA polymerase transcribes the coding sequence into mRNA, which is then trans-RNA spliced and translated into the protein encoded by the coding sequence.

A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene are generated. Preferably, the cloned gene is contained on a shuttl e vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast $2\mu$ plasmid.

This invention provides an agent which binds to the complex which modulates the fidelity of translation. Translation includes initiation, elongation, termination as well as degradation. In one embodiment, the agent inhibits ATPase/helicase activity, activity of MTT1, Upf1p; GTPase activity of eRF1 or eRF3; RNA binding; binding of the factors to the ribosome; or binding of the factors to each other. In another embodiment the agent modulates the binding of MTT1 to the polysome. In another embodiment the agent inhibits the binding of human MTT1 to eRF3. In another embodiment the agent facilitates the binding of human MTT1 to eRF3.

This invention provides an antibody which binds to the complex or MTT1. The antibody may be a monoclonal or polyclonal antibody. Further, the antibody may be labeled with a detectable marker that is either a radioactive, colorimetric, fluorescent, or a luminescent marker. The labeled antibody may be a polyclonal or monoclonal antibody. In one embodiment, the labeled antibody is a purified labeled antibody. Methods of labeling antibodies are well known in the art.

The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof.Such antibodies include but are not limited to polyclonal, monoclonal, chimeric, single chain, Fab fragments, and an Fab expression library. Further the protein or antibody may include a detectable marker, wherein the marker is a radioactive, colorimetric, fluorescent, or a luminescent marker.

Antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g, with radioisotopes (preferably technetium or iodine); magnetic resonance shift reagents (such as gadolinium and manganese); or radio-opaque reagents. The labels most commonly employed for these studies are radioactive elements, enzymes, chemicals which fluoresce when exposed to ultraviolet light, and others.A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The protein can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$ $^{90}Y$, $^{125}I$, $^{131}I$, $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

Complex specific antibodies and nucleic acids can be used as probes in methods to detect the presence of a complex polypeptide (using an antibody) or nucleic acid (using a nucleic acid probe) in a sample or specific cell type. In these methods, a complex-specific antibody or nucleic acid probe is contacted with a sample from a patient suspected of having a complex associated disorder, and specific binding of the antibody or nucleic acid probe to the sample detected. The level of the complex or nucleic acid present in the suspect sample can be compared with the level in a control sample, e.g., an equivalent sample from an unaffected individual to determine whether the patient has a complex-associated disorder. Complex polypeptides, or fragments thereof, can also be used as probes in diagnostic methods, for example, to detect the presence of complex-specific antibodies in samples. Additionally, complex-specific antibodies could be used to detect novel cofactors which have formed a complex with the complex or fragment thereof.

Presence, relative abundance, or absence of the complex is determined by the binding of the antibody. Possible detection methods including affinity chromatography, Western blotting, or other techniques well known to those of ordinary skill in the art. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule (see Marcus-Sekura, 1988, Anal. Biochem. 172:298). In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro (Marcus-Sekura, 1988, supra; Hambor et al., 1988, J. Exp. Med. 168:1237).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988, J. Am. Med. Assoc. 260:3030). Because they are sequence-specific, only mRNAs with particular sequences are inactivated.

Investigators have identified two types of ribozymes, Tetrahymena-type and "hammerhead"-type. Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

Any screening technique known in the art can be used to screen for agents that affect translation termination or a mRNA decay protein. The present invention contemplates screens for small molecule ligands.

Knowledge of the primary sequence of a translation termination or mRNA decay protein, and the similarity of that sequence with proteins of known function, can provide an initial clue as to agents that are likely to affect protein activity. Identification and screening of such agents is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

The screening can be performed with recombinant cells that express the proteins, complexes involved in translation termination or mRNA decay protein, or alternatively, with the purified protein. For example, the ability of labeled protein to bind to a molecule in a combinatorial library can be used as a screening assay, as described in the foregoing references.

This invention provides a method of screening a candidate host cell for the amount of the complex produced by said cell relative to a control cell, said method comprising: a) providing a clonal population of said candidate host cell; b) treating said clonal population of cells such that the intracellular proteins are accessible to an antibody; c) contacting said intracellular proteins with an antibody that specifically binds to the complex; and d) determining the relative amount of the complex produced by said candidate host cell.

The present invention further provides methods of screening the MTT1 gene to identify mutations. Such methods may further comprise the step of amplifying a portion of the MTT1 gene, and may further include a step of providing a set of polynucleotides which are primers for amplification of said portion of the MTT1 gene. The method is useful for identifying mutations for use in either diagnosis of the predisposition to, and diagnosis and treatment of megakaryocytic abnormality, hematopoetic disorders, myeloproliferative disorder, platelet disorder, leukemia; and prenatal diagnosis and treatment of tumors. Useful diagnostic techniques include, but are not limited to fluorescent in situ hybridization (FISH), direct DNA sequencing, PFGE analysis, Southern blot analysis, single stranded conformation analysis (SSCA), Rnase protection assay, allele-specific oligonucleotide (ASO), dot blot analysis and PCR-SSCP, as discussed in detail further below.

This invention provides a method of screening for a drug involved in peptidyl transferase activity during translation comprising: a) contacting cells with a candidate drug; and b) assaying for modulation of the complex, wherein a drug that modulates complex is involved in peptidyl transferase activity. Further, the complex may be assayed for NTPase activity, such as ATPase, GTPase, RNA binding acitivty, factors which bind to the complex, such as but not limited to eRF1 and eRF3, factors which dissociate from the ribosome, factors which promote aggregation; factors which enhance translation termination by slowing peptide hydrolysis.

This invention provides a method of screening for a drug active involved in enhancing translation termination comprising: a) contacting cells with a candidate drug; and b) assaying for modulation of the protein complex; wherein a drug that modulates protein complex is involved in enhancing translation termination.

This invention provides a method of screening for a drug involved in enhancing translation termination comprising: a) incubating the drug and the complex; and b) measuring the effect on nonsense suppression, thereby screening for a drug involved in enhancing translation termination. The assays may be a RNA binding or NTPase assays, such as ATPase, or GTPase assays which are known to those skilled in the art.

This invention provides a method for identifying a gene having a mutant allele comprising: (a) transfecting a cell with a MTT1 recombinant expression vector; (b) determining the phenotype of the cell after transfection; (c) comparing the cellular phenotype after transfection with the cellular phenotype before tranfection; and d) identifying the gene containing the mutant allele of the transfected cell.

This invention provides a method of identifying a test composition which modulates binding to MTT1, the method comprising: (a) incubating components comprising the test composition, and MTT1 wherein the incubating is carried out under conditions sufficient to permit the components to interact; and (b) measuring the effect of the test composition on the binding to MTT1. In one embodiment the method further comprising identifying a gene comprising; (a) introducing into a cell a test composition which modulates binding to MTT1; (b) determining the phenotype of the cell after (a); (c) comparing the cellular phenotype after (a) with the cellular phenotype before (a); and (d) identifying the gene of the cell into which the test composition has been introduced.

A "test composition", as used herein, is any composition such as a gene, a nucleic acid sequence, a polypeptide, peptide fragment or composition created through the use of a combinatorial library or other combinatorial process that can be assayed for its ability to function in given capacity or compound which mimics the activity of the complex. Often such a test composition, nucleic acid sequence or polypeptide is, because of its sequence or structure, suspected of being able to function in a given capacity.

A "co-factor" is any composition (e.g., a polypeptide, polypeptide derivative, or peptidomimetic) that is capable of modulating the complex and influencing NMD or efficiency of translation termination. Included are compositions that naturally induce NMD or the efficiency or fidelity of translation termination via the complex; also included are compositions that do not naturally induce NMD (e.g., artificial compositions and natural compositions that serve other purposes).

The term "agonist" as used herein means any composition that is capable of increasing or stimulating the efficiency or fidelity of translation termination or mRNA degradation by interacting with or binding to the complex or factors, such as eRf3 or, upf1, of the complex which interact with MTT1 of the complex. The term "antagonist" as used herein means any composition that is capable of decreasing the efficiency or fidelity of translation termination or mRNA degredation by interacting with or binding to the complex, MTT1, or factors, such as eRf3 or upf1, of the complex which interact with MTT1 of the complex.

Identification and isolation of a gene encoding a MTT1 of the invention provides for expression of MTT1 in quantities greater than can be isolated from natural sources, or in indicator cells that are specially engineered to indicate the activity of MTT1 expressed after transfection or transformation of the cells. Accordingly, in addition to rational design of agonists and antagonists based on the structure of MTT1, the present invention contemplates an alternative method for identifying specific ligands of MTT1 using various screening assays known in the art.

Any screening technique known in the art can be used to screen for MTT1 agonists or antagonists. The present invention contemplates screens for small molecules that bind to MTT1 and agonize or antagonize MTT1 in vitro and/or in vivo. For example, natural products libraries can be screened using assays of the invention for molecules that agonize or antagonize the activity of MTT1.

Knowledge of the primary sequence of the MTT1, and the similarity of that sequence with other DNA binding proteins, can provide an initial clue as the inhibitors or antagonists of the MTT1. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, *Science* 249:386–390 (1990); Cwirla, et al., *Proc. Natl. Acad. Sci.*, 87:6378–6382 (1990); Devlin et al., *Science*, 249:404–406 (1990)], very large libraries can be constructed ($10^6$–$10^8$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [*14th International Congress of Biochemistry, Volume 5*, Abstract FR:013 (1988); Furka, *Int. J. Peptide Protein Res.* 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in its entirety], and the like can be used to screen for MTT1 ligands according to the present invention.

Screening can be performed with recombinant cells that express the MTT1, or alternatively, using purified protein, and/or specific structural/functional domains of MTT1s e.g., produced recombinantly, as described above. For example, a labeled MTT12 dimerization domain can be used to screen libraries, as described in the foregoing references for small molecules that will inhibit the dimerization of the MTT12.

The invention also provides a method for detecting novel co-factors or inhibitors which bind MTT1 which comprises contacting a sample comprising MTT1 with test compositions and measuring the change in NMRD after application of the test composition. The MTT1 protein of the instant invention is useful in a screening method for identifying novel test compounds or novel test compositions which affect NMRD via MTT1. Thus, in another embodiment, the invention provides a method for screening test compositions comprising incubating components, which include the test composition, and MTT1 under conditions sufficient to allow the components to interact, then subsequently measuring the effect the test composition has on NMRD in a test cell. The observed effect on NMD between MTT1 and a composition may be either agonistic or antagonistic. Preferably, the polypeptide encoding the MTT1 is the polypeptide or a synthetic peptide which has the biological activity of the MTT1 protein.

Because MTT1 is closely related to the UPF1 family in yeast, the term "MTT1-specific probe", in the context of this invention, refers to probes that bind to nucleic acids encoding MTT1 polypeptides, or to complementary sequences thereof, to a detectably greater extent than to nucleic acids encoding UPF1 sequences, or to complementary sequences thereof. The term "MTT1-specific probe" thus includes probes that can bind to nucleic acids encoding MTT1 polypeptides (or to complementary sequences thereof), but not to nucleic acids encoding PF sequences (or to complementary sequences thereof), to an appreciable extent.

The invention facilitates production of MTT1-specific nucleic acid probes. Methods for obtaining such probes can be designed based on the amino acid sequence alignments shown in FIG. 1. The probes, which can contain at least 9, e.g., at least 12, 15, 25, 35, 50, 100, or 150 nucleotides, can be produced using any of several standard methods (see, e.g., Ausubel, et al., supra). For example, preferably, the probes are generated using PCR amplification methods, such as those described below. In these methods, primers are designed that correspond to MTT1 sequences, which can include MTT1-specific amino acids, and the resulting PCR product is used as a probe to screen a nucleic acid library, such as a cDNA library.

The MTT1-specific nucleic acid probes can be labeled with a compound that facilitates detection of binding to the MTT1 nucleic acid in the sample. For example, the probe can contain biotinylated nucleotides, to which detectably labeled avidin conjugates (e.g., horse-radish peroxidase-conjugated avidin) can bind. Radiolabeled nucleic acid probes can also be used. These probes can be used in nucleic acid hybridization assays to detect altered levels of MTT1s in a sample. For example, in situ hybridization, RNASE protection, and Northern Blot methods can be used. Other standard nucleic acid detection methods that can be used in the invention are known to those of skill in the art (see, e.g., Ausubel et al., supra). In addition, when the diagnostic molecule is a nucleic acid, it can be amplified prior to binding with a MTT1-specific probe. Preferably, PCR is used, but other nucleic acid amplification methods, such as the ligase chain reaction (LCR), ligated activated transcription (LAT), and nucleic acid sequence-based amplification (NASBA) methods can be used.

The invention also provides a method for determining whether a test agent or composition modulates the complex in a cell. The method can be performed by (i) providing a cell that has the complex; (ii) contacting the cell with a test agent or composition that, in the absence of the test agent or composition, activates the complex in the cell; and (iii) detecting a change in the complex of the cell. In practicing the invention, the cell can be contacted with the test agent or composition either simultaneously or sequentially. An increase in the complex indicates that the test agent or composition is an agonist of the complex while a decrease in the complex indicates that the test agent or composition is an antagonist of the complex. If desired, the above-described method for identifying modulators of the complex can be used to identify compositions, co-factors or other compositions within the complex pathway comprising the complex for use in this aspect of the invention. Any agent or composition can be used as a test agent or composition in practicing the invention; a preferred test agent or compositions include polypeptides and small organic agent or compositions. Although sequence or structural homology can provide a basis for suspecting that a test agent or composition can modulate the complex in a cell, randomly chosen test agent or compositions also are suitable for use in the invention. Art-known methods for randomly generating an agent or compositions (e.g., expression of polypeptides from nucleic acid libraries) can be used to produce suitable test agent or compositions. Those skilled in the art will recognize alternative techniques can be used in lieu of the particular techniques described herein.

The invention also provides a method for detecting novel co-factors or inhibitors which bind the complex which comprises contacting a sample comprising the complex with test compositions and measuring the change in the complex after application of the test composition. The complex of the instant invention is useful in a screening method for identifying novel test compounds or novel test compositions which affect the complex. Thus, in another embodiment, the invention provides a method for screening test compositions comprising incubating components, which include the test composition, and the complex under conditions sufficient to allow the components to interact, then subsequently measuring the effect the test composition has on the complex in a test cell. The observed effect on the complex and a composition may be either agonistic or antagonistic.

This invention provides a method of modulating peptidyl transferase activity during translation, comprising contacting a cell with the complex in an amount effective to facilitate translation termination, thereby modulating the peptidyl transferase activity. This invention provides a method of modulating peptidyl transferase activity during translation, comprising contacting a cell with the agent, in an amount effective to suppress nonsense translation termination, thereby modulating the peptidyl transferase activity. The peptidyl transferase activity during translation occurs during initiation, elongation, termination and degradation of mRNA.

This invention provides a method of modulating the efficiency of translation termination of mRNA at a nonsense codon and/or promoting degradation of aberrant transcripts, comprising contacting a cell with the agent, in an amount effective to inhibit the binding of Mtt1 and eRF3, thereby modulating the efficiency of translation termination of mRNA at a nonsense codon and/or promoting degradation of aberrant transcripts.

This invention provides a method of modulating the efficiency of translation termination of mRNA at a nonsense codon and/or promoting degradation of aberrant transcripts, comprising contacting a cell with an agent, which inhibits the ATPase/helicase activity of MTT1, thereby modulating the efficiency of translation termination of mRNA at a nonsense codon and/or promoting degradation of aberrant transcripts.

This invention provides a method of modulating the efficiency of translation termination of mRNA at a nonsense codon and/or promoting degradation of aberrant transcripts, comprising contacting a cell with an agent, which inhibits the ATPase/helicase activity of MTT1 to eRF3, thereby modulating the efficiency of translation termination of mRNA at a nonsense codon and/or promoting degradation of aberrant transcripts As defined herein, "modulation" of translation fidelity means to alter the activity of the translational apparatus in order to increase or decrease the fidelity of the reaction without completely inhibiting the process. For example, modulating the translation termination process at a nonsense codon occurs as a consequence of altering the ability of the translation release factors at termination codon to promote peptidyl release when in competition with near cognate tRNAs. The end result would be that the near cognate tRNA is incorporated into the polypeptide chain and termination is suppressed. Since most proteins only need to be expressed to 5% to 20% of wild-type levels, translation termination does not need to be inhibited. One needs to modulate the termination process such that it is less efficient by a small amount.

In a specific embodiment, agents that interfere with NTPase activity, such as, ATPase activity, GTPase, helicase activity, or zinc finger motif configuration may be selected for testing. Such agents may be useful drugs for treating viral infections, since many retroviruses, notably HIV, coronaviruses, and other RNA viruses that are associated with medical and veterinary pathologies. By providing the identity of proteins that modulate frameshifting events, an initial screen for agents may include a binding assay to such proteins. This assay may be employed for testing the effectiveness of agents on the activity of frameshift associated proteins from human as well as yeast or other non-human source, including but not limited to animals.

For example, identification of agents that inhibit the decay pathway, stabilize nonsense transcripts or modulate the efficiency of translation termination are important for the success of antisense RNA technology. Antisense RNAs are small, diffusible, untranslated and highly structured transcripts that pair to specific target RNAs at regions of complementarity, thereby controlling target RNA function or expression. However, attempts to apply antisense RNA technology have met with limited success. The limiting factor appears to be in achieving sufficient concentrations of the antisense RNA in a cell to inhibit or reduce the expression of the target gene. It is likely that one impediment to achieving sufficient concentration is the nonsense decay pathway, since the short antisense RNA transcripts, which are not meant to encode a gene product, will likely lead to rapid translation termination if translation occurs, and consequently to rapid degradation and low abundance of the antisense RNA in the cell. Thus, the agents of the invention that stabilize aberrant mRNA transcripts may also stabilize antisense RNAs.

This invention provides a method of modulating the efficiency of translation termination of mRNA and/or degradation of aberrant transcripts in a cell, said method comprising: a) providing a cell containing a vector comprising the nucleic acid encoding the complex; or an antisense thereof; b) overexpressing said nucleic acid vector in said cell to produce an overexpressed complex so as to interfere or inhibit with the function of the complex.

This invention provides a method for determining whether a subject carries a mutation in the MTT1 gene which comprises: a) obtaining an appropriate nucleic acid sample from the subject; and(b) determining whether the nucleic acid sample from step (a) is, or is derived from, a nucleic acid which encodes mutant MTT1 so as to thereby determine whether a subject carries a mutation in the MTT1 gene. In one embodiment, the nucleic acid sample in step (a) comprises mRNA corresponding to the transcript of DNA encoding a mutant MTT1, and wherein the determining of step (b) comprises: (i) contacting the mRNA with the oligonucleotide under conditions permitting binding of the mRNA to the oligonucleotide so as to form a complex; (ii) isolating the complex so formed; and (iii) identifying the mRNA in the isolated complex so as to thereby determine whether the mRNA is, or is derived from, a nucleic acid which encodes mutant MTT1. In another embodiment, the determining of step (b) comprises: i) contacting the nucleic acid sample of step (a), and the isolated nucleic acid with restriction enzymes under conditions permitting the digestion of the nucleic acid sample, and the isolated nucleic acid into distinct, distinguishable pieces of nucleic acid; (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes mutant MTT1.

This invention provides a transgenic nonhuman mammal which comprises at least a portion of nucleic acid encoding MTT1 gene and Upf1p introduced into the mammal at an embryonic stage. Methods of producing a transgenic non-human mammal are known to those skilled in the art.

This invention provides a method of detecting a disorder associated with the expression of mtt1, wherein the method comprises contacting a sample from a subject having or suspected of having a disorder with a reagent that detects expression of the mtt1 and detecting the binding of the reagent in the sample.

This invention provides method for identifying a disease state involving a defect in the complex of claim 1 comprising: (a) transfecting a cell with a nucleic acid which encodes the complex; (b) determining the proportion of the defective complex of the cell after transfection; (c) comparing the proportion of the defective complex of the cell after transfection with the proportion of defective complex of the cell before transfection.

As noted above, nonsense-mediated mRNA decay leads to cellular deficiencies of essential proteins and hence to disease. Altered control of the stability of normal mRNAs can have comparably dire consequences.

This invention provides a method for treating a disease associated with peptidyl transferase activity, comprising administering to a subject a therapeutically effective amount of a pharmaceutical composition comprising the complex of claim 1 or the agents which modulate or stimulate the complex, and a pharmaceutical carrier or diluent, thereby treating the subject.

Nonsense mutations cause approximately 20–40% of the individual causes of over 240 different inherited diseases (including cystic fibrosis, hemophilia, familial hypercholesterolemia, retinitis pigmentosa, Duchenne muscular dystrophy, and Marfan syndrome). For many diseases in which only one percent of the functional protein is produced, patients suffer serious disease symptoms, whereas boosting expression to only five percent of normal levels can greatly reduce the severity or eliminate the disease. In addition, a remarkably large number of the most common forms of colon, breast, esophageal, lung, head and neck, bladder cancers result from frameshifting and nonsense mutations in regulatory genes (i.e., p53, BRCA1, BRCA2, etc.). Correcting nonsense mutations in the regulatory genes to permit synthesis of the respective proteins should cause death of the cancer cells.

A large number of observations point to an important role for protein synthesis in the fidelity of translation termination and the mRNA decay process. In fact, it appears that these two processes have co-evolved and that factors essential for one process also function in the other. Evidence for this linkage includes experiments demonstrating that: a) drugs or mutations that interfere with translational elongation promote mRNA stabilization, b) sequence elements that dictate rapid mRNA decay can be localized to mRNA coding regions and the activity of such elements depends on their translation, c) degradative factors can be ribosome-associated, and d) premature translational termination can enhance mRNA decay rates Since the quantity of a particular protein synthesized in a given time depends on the cellular concentration of its mRNA it follows that the regulation of mRNA decay rates provides a powerful means of controlling gene expression. In mammalian cells, mRNA decay rates (expressed as half-lives) can be as short as 15–30 minutes or as long as 500 hours. Obviously, such differences in mRNA decay rates can lead to as much as 1000-fold differences in the level of specific proteins. An additional level of control is provided by the observation that decay rates for individual mRNAs need not be fixed, but can be regulated as a consequence of autogenous feedback mechanisms, the presence of specific hormones, a particular stage of differentiation or the cell-cycle, or viral infection.

Perhaps the best examples of the integration of translation and mRNA decay are studies documenting the consequences of premature translational termination. This occurs when deletion, base substitution, or frameshift mutations in DNA lead to the synthesis of an mRNA that contains an inappropriate stop codon (nonsense codon) within its protein coding region. The occurrence of such a premature stop codon arrests translation at the site of early termination and causes the synthesis of a truncated protein. Regardless of their "normal" decay rates, mRNAs transcribed from genes that harbor nonsense mutations (dubbed "nonsense-containing mRNAs"are degraded very rapidly. Such "nonsense-mediated mRNA decay" is ubiquitous, i.e., it has been observed in all organisms tested, and leads to as much as ten-to one hundred-fold reduction in the abundance of specific mRNAs. The combination of severely reduced mRNA abundance and prematurely terminated translation causes reductions in the overall level of expression of specific genes that are as drastic as the consequences of gene deletion. The importance of nonsense-mediated mRNA decay to human health is illustrated by the identification of a growing number of inherited disease in which nonsense mutations cause the disease state and in which nonsense mutations cause the disease state and in which the respective mRNAs have been shown to be substrates of the nonsense-mediated mRNA decay pathway.

An important point, is that inactivation of the nonsense-mediated mRNA decay pathway can be accomplished without impeding cellular growth and leads to the restoration of normal levels and normal decay rates for nonsense-containing mRNA's. More significantly, the yeast experiments (and others) demonstrate that, although an mRNA may still contain a nonsense codon, inactivation of this decay pathway allows enough functional protein to be synthesized that cells can overcome the original genetic defect. Thus, it is possible to treat diseases causes by nonsense mutations by downregulating the nonsense-mediated mRNA decay pathway.

The disease, proteins, or genes which are as a result of nonsense or frameshift mutations include but are not limited to the following: HEMOGLOBIN—BETA LOCUS; CYSTIC FIBROSIS TRANSMEMBRANE CONDUCTANCE REGULATOR; MUSCULAR DYSTROPHY, PSEUDO-HYPERTROPHIC PROGRESSIVE, DUCHENNE AND BECKER, TYPES; PHENYLKETONURIA, INSULIN RECEPTOR; HEMOPHILIA A, ADENOMATOUS POLYPOSIS OF THE COLON, HYPERCHOLESTEROLEMIA, FAMILIAL, NEUROFIBROMATOSIS, TYPE I, HEMOPHILIA B, HYPERLIPOPROTEINEMIA TYPE I, TAY-SACHS DISEASE, BREAST CANCER TYPE I, ADRENAL HYPERPLASIA, VON WILLEBRAND DISEASE, MUCOPOLYSACCHARIDOSIS TYPE I, ALBINISM I, POLYCYSTIC KIDNEY DISEASE 1, ORNITHINE AMINOTRANSFERASE DEFICIENCY ANGIOKERATOMA, DIFFUSE MULTIPLE ENDOCRINE NEOPLASIA TYPE I, SEX-DETERMINING REGION Y, SOLUTE CARRIER FAMILY 4 ANION EXCHANGER MEMBER 1, COLLAGEN TYPE I ALPHA-1 CHAIN, HYPOXANTHINE GUANINE PHOSPHORIBOSYLTRANSFERASE 1, GLUCOKINASE, TUMOR PROTEIN p53, PROTEOLIPID PROTEIN, MYELIN, GROWTH HORMONE RECEPTOR, LUTEINIZING HORMONE/CHORIOGONADOTROPIN RECEPTOR;, APOLIPOPROTEIN A-I OF HIGH DENSITY LIPOPROTEIN, GLUCOSE-6-PHOSPHATE DEHYDROGENASE, ORNITHINE TRANSCARBAMYLASE DEFICIENCY HYPERAMMONEMIA, XERODERMA PIGMENTOSUM I, PAIRED BOX HOMEOTIC GENE 6, VON HIPPEL-LINDAU SYNDROME, CYCLIN-DEPENDENT KINASE INHIBITOR 2A, TUBEROUS SCLEROSIS 2, TYROSINEMIA, TYPE I NORRIE DISEASE, PHOSPHODIESTERASE 6B, PALMITOYL-PROTEIN THIOESTERASE, APOLIPOPROTEIN B, BRUTON AGAMMAGLOBULINEMIA TYROSINE KINASE, ADRENAL HYPOPLASIA, SOLUTE CARRIER FAMILY 5, 5,10-2METHYLENETETRAHYDROFOLATE REDUCTASE, WILMS TUMOR, POLYCYSTIC KIDNEYS, TRANSCRIPTION FACTOR 14, HEPATIC NUCLEAR FACTOR, MUCOPOLYSACCHARIDOSIS TYPE II, PROTEIN C DEFICIENCY, CONGENITAL THROMBOTIC DISEASE DUE TO NEUROFIBROMATOSIS TYPE II, ADRENOLEUKODYSTROPHY, COLLAGEN TYPE VII ALPHA-1, COLLAGEN, TYPE X ALPHA 1, HEMOGLOBIN—ALPHA LOCUS-2, GLYCOGEN STORAGE DISEASE VII, FRUCTOSE INTOLERANCE, BREAST CANCER 2 EARLY-ONSET; BRCA2, FUCOSYLTRANSFERASE 2, HERMANSKY-PUDLAK SYNDROME, THYROGLOBULIN, RETINOBLASTOMA, WISKOTT-ALDRICH SYNDROME, RHODOPSIN, COLLAGEN TYPE XVII, CHOLINERGIC RECEPTOR, CYCLIC NUCLEOTIDE GATED CHANNEL, PHOTORECEPTOR, cGMP GATED, CHOLINERGIC RECEPTOR NICOTINIC EPSILON POLYPEPTIDE, RECOMBINATION ACTIVATING GENE-1, CAMPOMELIC DYSPLASIA, IMMUNODEFICIENCY WITH INCREASED IgM, RET PROTOONCOGENE; RET MUCOPOLYSACCHARIDOSIS TYPE IVA, LEPTIN RECEPTOR, SPHEROCYTOSIS, HEREDITARY, ARGININE VASOPRESSIN, APOLIPOPROTEIN C-II DEFICIENCY TYPE I HYPERLIPOPROTEINEMIA DUE TO CYSTIC FIBROSIS, WILSON DISEASE, LEPTIN, ANGIONEUROTIC EDEMA, CHLORIDE CHANNEL 5, GONADAL DYSGENESIS, PORPHYRIA, ACUTE INTERMITTENT, HEMOGLOBIN, GAMMA A, KRABBE DISEASE, GLYCOGEN STORAGE DISEASE V, METACHROMATIC LEUKODYSTROPHY, LATE-INFANTILE, GIANT PLATELET SYNDROME, VITAMIN D RECEPTOR, SARCOGLYCAN, DELTA, TWIST, DROSOPHILA, ALZHEIMER DISEASE, OSTEOPETROSIS WITH RENAL TUBULAR ACIDOSIS, AMELOGENESIS IMPERFECTA-1, HYPOPLASTIC TYPE, POU DOMAIN, CLASS 1, TRANSCRIPTION FACTOR 1, DIABETES MELLITUS, AUTOSOMAL DOMINANT V-KIT HARDY-ZUCKERMAN 4 FELINE SARCOMA VIRAL ONCOGENE HOMOLOG, HEMOGLOBIN—DELTA LOCUS, ADENINE PHOSPHORIBOSYLTRANSFERASE, PHOSPHATASE AND TENSIN HOMOLOG, GROWTH HORMONE 1, CATHEPSIN K, WERNER SYNDROME, NIEMANN-PICK DISEASE, GROWTH HORMONE-RELEASING HORMONE RECEPTOR, CERULOPLASMIN, COLONY STIMULATING FACTOR 3 RECEPTOR, GRANULOCYTE, PERIPHERAL MYELIN PROTEIN 22, FUCOSIDOSIS, EXOSTOSES MULTIPLE TYPE II, FANCONI ANEMIA, COMPLEMENTATION GROUP C, ATAXIA-TELANGIECTASIA, CADHERIN 1, SOLUTE CARRIER FAMILY 2, MEMBER 2, UDP GLUCURONOSYLTRANSFERASE 1 FAMILY, A1, TUBEROUS SCLEROSIS 1, LAMININ, GAMMA 2, CYSTATIN B, POLYCYSTIC KIDNEY DISEASE 2, MICROSOMAL TRIGLYCERIDE TRANSFER PROTEIN, 88 KD, DIASTROPHIC DYSPLASIA, FLAVIN-CONTAINING MONOOXYGENASE 3, GLYCOGEN STORAGE DISEASE III, POU DOMAIN, CLASS 3, TRANSCRIPTION FACTOR 4, CYTOCHROME P450, SUBFAMILY IID, PORPHYRIA, CONGENITAL ERYTHROPOIETIC, ATPase, Cu(2+)-TRANSPORTING, ALPHA POLYPEPTIDE, COLON CANCER, FAMILIAL, NON-POLYPOSIS TYPE I, PHOSPHORYLASE KINASE, ALPHA 1 SUBUNIT (MUSCLE), ELASTIN, CANAVAN DISEASE EXCISION-REPAIR, COMPLEMENTING DEFECTIVE, IN CHINESE HAMSTER, 5, JANUS KINASE 3, STEROIDOGENIC ACUTE REGULATORY PROTEIN, FUCOSYLTRANSFERASE 6, GLAUCOMA 1, OPEN ANGLE, EXOSTOSES, MULTIPLE, TYPE I, MYOCILIN, AGRANULOCYTOSIS, INFANTILE GENETIC ERYTHROPOIETIN RECEPTOR, SURVIVAL OF MOTOR NEURON 1, TELOMERIC, SONIC HEDGEHOG, DROSOPHILA, HOMOLOG OF, LECITHIN:CHOLESTEROL ACYLTRANSFERASE DEFICIENCY, POSTMEIOTIC SEGREGATION INCREASED (S. CEREVISIAE)-1, EXCISION-REPAIR CROSS-COMPLEMENTING RODENT REPAIR DEFICIENCY, GROUP 6, MAPLE SYRUP URINE DISEASE APOPTOSIS ANTIGEN 1, TRANSCRIPTION FACTOR 1, HEPATIC, UBIQUITIN-PROTEIN LIGASE E3A, TRANSGLUTAMINASE 1, MYOSIN VIIA, GAP JUNCTION PROTEIN, BETA-1, 32-KD, TRANSCRIPTION FACTOR 2, HEPATIC, PROTEIN 4.2, ERYTHROCYTIC, THYROID-STIMULATING HORMONE, BETA CHAIN, TREACHER COLLINS-FRANCESCHETTI SYNDROME 1, CHOROIDEREMIA, ENDOCARDIAL FIBROELASTOSIS-2, COWDEN DISEASE, ANTI-MULLERIAN HORMONE, SRY-BOX 10, PTA DEFI- CIENCY TYROSINASE-RELATED PROTEIN 1, PHOSPHORYLASE KINASE, BETA SUBUNIT, SERINE/THREONINE PROTEIN KINASE 11, PHOSPHOLIPASE A2, GROUP IIA, EXCISION-REPAIR, COMPLEMENTING DEFECTIVE, IN CHINESE HAMSTER 3, ADRENAL HYPERPLASIA II COLLAGEN, TYPE IV, ALPHA-4 CHAIN, THROMBASTHENIA OF GLANZMANN AND NAEGELI RETINAL PIGMENT EPITHELIUM-SPECIFIC PROTEIN, 65-KD, HOMEO BOX A13, CALPAIN, LARGE POLYPEPTIDE L3, XANTHINURIA LAMININ, ALPHA 2, CYTOCHROME P450, SUBFAMILY XIX, MUCOPOLYSACCHARIDOSIS TYPE VI, CEROID-LIPOFUSCINOSIS, NEURONAL 3, JUVENILE, CITRULLINEMIA MYOCLONUS EPILEPSY OF UNVERRICHT AND LUNDBORG PHOSPHORYLASE KINASE, TESTIS/LIVER, GAMMA 2, SOLUTE CARRIER FAMILY 3, MEMBER 1, PTERIN-4-ALPHA-CARBINOLAMINE DEHYDRATASE, ALBINISM, OCULAR, TYPE I, LEPRECHAUNISM EPILEPSY, BENIGN NEONATAL, HIRSCHSPRUNG DISEASE OSTEOPETROSIS, AUTOSOMAL RECESSIVE RAS p21 PROTEIN ACTIVATOR 1, MUCOPOLYSACCHARIDOSIS TYPE VII CHEDIAK-HIGASHI SYNDROME, POTASSIUM CHANNEL, INWARDLY-RECTIFYING, SUBFAMILY J, MEMBER 1, PLAKOPHILIN 1, PLATELET-ACTIVATING FACTOR ACETYLHYDROLASE ISOFORM 1B, ALPHA SUBUNIT, PLECTIN 1, SHORT STATURE, MHC CLASS II TRANSACTIVATOR, HYPOPHOSPHATEMIA, VITAMIN D-RESISTANT RICKETS, RIEG BICOID-RELATED HOMEOBOX TRANSCRIPTION FACTOR 1, MUSCULAR DYSTROPHY, LIMB-GIRDLE, TYPE 2E, RETINITIS PIGMENTOSA-3, MutS, E. COLI, HOMOLOG OF, 3, TYROSINE TRANSAMINASE DEFICIENCY LOWE OCULOCEREBRORENAL SYNDROME, XANTHISM NEPHRONOPHTHISIS, FAMILIAL JUVENILE 1, HETEROTAXY, VISCERAL, X-LINKED MILLER-DIEKER LISSENCEPHALY SYNDROME, PROPERDIN DEFICIENCY, X-LINKED 3-2OXOACID CoA TRANSFERASE, WAARDENBURG-SHAH SYNDROME MUSCULAR DYSTROPHY, LIMB-GIRDLE, TYPE 2, ALPORT SYNDROME, AUTOSOMAL RECESSIVE GLYCOGEN STORAGE DISEASE IV DIABETES MELLITUS, AUTOSOMAL DOMINANT, TYPE II SOLUTE CARRIER FAMILY 2, MEMBER 1, HAND-FOOT-UTERUS SYNDROME CYSTINOSIS, EARLY-ONSET OR INFANTILE NEPHROPATHIC TYPE, CRIGLER-NAJJAR SYNDROME INSULINLIKE GROWTH FACTOR 1, LACTATE DEHYDROGENASE-A, STICKLER SYNDROME, TYPE II, AMAUROSIS CONGENITA OF LEBER I ALPHA-GALACTOSIDASE B, ADRENAL HYPERPLASIA I LI-FRAUMENI SYNDROME, SOLUTE CARRIER FAMILY 12, MEMBER 1, KLEIN-WAARDENBURG SYNDROME PEROXISOME BIOGENESIS FACTOR 7, PAIRED BOX HOMEOTIC GENE 8, RETINOSCHISIS, 5-HYDROXYTRYPTAMINE RECEPTOR 2C, URATE OXIDASE, PEUTZ-JEGHERS SYNDROME MITRAL VALVE PROLAPSE, FAMILIAL, MELANOMA, CUTANEOUS MALIGNANT, 2, FUCOSYLTRANSFERASE 1, PYCNODYSOSTOSIS, MUCOPOLYSACCHARIDOSIS TYPE IIIB P-GLYCOPROTEIN-3, SEVERE COMBINED IMMUNODEFICIENCY, B-CELL-NEGATIVE RETINITIS PIGMENTOSA, RIBOSOMAL PROTEIN S6 KINASE, 90 KD, POLYPEPTIDE 3, SYNDROME SYNDROME, FACTOR DEFICIENCY X-LINKED, AGAINST DECAPENTAPLEGIC, DROSOPHILA, HOMOLOG OF, 4, FACTOR FOR COMPLEMENT, DEHYDROGENASE/DELTA-ISOMERASE, TYPE I CONDUCTIVE, WITH STAPES FIXATION AQPI 1, PROGRESSIVE, PROGRESSIVE FAMILIAL INTRAHEPATIC, TYPE III MONOPHOSPHATE DEAMINASE-1, HOMEO BOX TRANSCRIPTION FACTOR 1.

This invention provides methods to screen drugs which acts as therapeutics that treat diseases caused by nonsense and frameshift mutations. By biochemical and in vitro assays which monitor the activity of ATP binding, ATPase activity, RNA helicase activity, GTP binding, GTPase activity, release factors, or RNA binding to the complex or to each other (i.e. MTT1 to eRF3); developing assays capable of quantitating the activity of the human gene product in mRNA decay and translational suppression; screening compounds using aforementioned assays. The experiments disclosed herein have shown that antagonizing/agonizing the activity of the complex of factors, proteins of the complex can overcome the otherwise lethal effects of nonsense mutations in essential genes or and have established yeast as a model system for drug development for which human agents or compounds may be obtained.

This invention provides a method for identifying a disease state involving defective the protein complex comprising: (a) transfecting a cell with a nucleic acid which encodes the protein complex; (b) determining the proportion of the defective protein complex of the cell after transfection; (c) comparing the proportion of the defective protein complex of the cell after transfection with the proportion of defective protein complex of the cell before transfection.

This invention provides method for identifying a disease state involving defective multimeric proteins comprising: (a) transfecting a cell with the vector of claim ; (b) determining the proportion of defective multimeric proteins of the cell after tansfection; (c) comparing the proportion of defective multimeric proteins of the cell after transfection with the proportion of defective multimeric proteins of the cell before transfection.

This invention provides a method of identifying genes which are involved in modulation of translation termination, which comprises: a) isolated a gene of interest; and b) determining whether the gene of interest comprises motifs I–IX, wherein if the gene comprises any one of the nine motifs the gene modulates translation termination. In one embodiment motif I comprises the sequence: GppGTKTxT-X(n) (SEQ ID NO:1). In another embodiment motif II comprises the sequence riLxcaSNxAvDxl-X(n) (SEQ ID NO:2). In another embodiment motif III comprises the sequence vviDExxQaxxxxxiPi-X(n) (SEQ ID NO:3). In another embodiment motif IV comprises the sequence xxil aGDxxQLp-X(n) (SEQ ID NO:4). In another embodiment motif V comprises the sequence 1xx SLF erv-X(n) (SEQ ID NO:5). In another embodiment motif VI comprises the sequence LxxQYRMhpxisefpxYxgxL-X(n) (SEQ ID NO:6). In another embodiment motif VII comprises the sequence IgvitPYxxQvxxl-X(n) (SEQ ID NO:7). In another embodiment motif VIII comprises the sequence vevx-tVDxFQGreKdxlilSc VR-X(n) (SEQ ID NO:8). In another embodiment motif IX comprises the sequence iGFLxdxR-RINVaITRak. Capitol letters represent a position in the primary sequence whose specific amino acid residue is very highly conserved among member of this group. Lowercase letters represent a position in the primary sequence whose chemical properties are conserved but not necessarily the exact identity.

There are several methods that can be used to detect DNA sequence variation. Direct DNA sequencing, either manual sequencing or automated fluorescent sequencing can detect sequence variation. For a gene as large as MTT1, manual sequencing is very labor-intensive, but under optimal conditions, mutations in the coding sequence of a gene are rarely missed. Another approach is the single-stranded conformation polymorphism assay (SSCA) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation.

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of tumors. Southern blots displaying hybridizing fragments (differing in length from control DNA when probed with sequences near or including the MTT1 gene) indicate a possible mutation. If restriction enzymes which produce very large restriction fragments are used, then pulsed field gel electrophoresis (PFGE) is employed.

Detection of point mutations may be accomplished by molecular cloning of the MTT1 allele(s) and sequencing the allele(s) using techniques well known in the art. Alternatively, the gene sequences can be amplified directly from a genomic DNA preparation from the tumor tissue, using known techniques. The DNA sequence of the amplified sequences can then be determined. There are six well known methods for a more complete, yet still indirect, test for confirming the presence of a susceptibility allele: 1) single stranded conformation analysis (SSCA) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Rano & Kidd, 1989). For allele-specific PCR, primers are used which hybridize at their 3' ends to a particular MTT1 mutation. If the particular MTT1 mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the MTT1 mutation found in that individual. Other techniques for detecting insertions and deletions as known in the art can be used.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the MTT1 gene can also be detected using Southern hybridization, especially if the changes are gross rearrangements, such as deletions and insertions.

DNA sequences of the MTT1 gene which have been amplified by use of PCR may also be screened using allele-specific probes. These probes are nucleic acid oligomers, each of which contains a region of the MTT1 gene sequence harboring a known mutation. For example, one oligomer may be about 30 nucleotides in length, corresponding to a portion of the MTT1 gene sequence. By use of a battery of such allele-specific probes, PCR amplification products can be screened to identify the presence of a previously identified mutation in the MTT1 gene. Hybridization of allele-specific probes with amplified MTT1 sequences can be performed, for example, on a nylon filter. Hybridization to a particular probe under stringent hybridization conditions indicates the presence of the same mutation as in the allele-specific probe.

Alteration of MTT1 mRNA expression can be detected by any techniques known in the art. These include Northern blot analysis, PCR amplification and RNase protection. Diminished mRNA expression indicates an alteration of the wild-type MTT1 gene. Alteration of wild-type MTT1 genes can also be detected by screening for alteration of wild-type MTT1 protein. For example, monoclonal antibodies immunoreactive with MTT1 can be used to screen a tissue. Lack of cognate antigen would indicate a MTT1 mutation. Antibodies specific for products of mutant alleles could also be used to detect mutant MTT1 gene product. Such immunological assays can be done in any convenient formats known in the art. These include Western blots, immunohistochemical assays and ELISA assays. Any means for detecting an altered MTT1 protein can be used to detect alteration of wild-type MTT1 genes. Functional assays, such as protein binding determinations, can be used. In addition, assays can be used which detect MTT1 biochemical function. Finding a mutant MTT1 gene product indicates alteration of a wild-type MTT1 gene. Mutant MTT1 genes or gene products can also be detected in other human body samples, such as serum, stool, urine and sputum.

The present invention also provides for fusion polypeptides, comprising MTT1 polypeptides and fragments. Homologous polypeptides may be fusions between two or more MTT1 polypeptide sequences or between the sequences of MTT1 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial beta-galactosidase, trpe, protein A, beta-lactamase, alpha amylase, alcohol dehydrogenase and yeast alpha mating factor. See, e.g., Godowski et al. , 1988. Fusion proteins will typically be made by either recombinant nucleic acid methods, as described below, or may be chemically synthesized. Techniques for the synthesis of polypeptides are described, for example, in Merrifield, 1963.

The diagnostic assays of the invention can be nucleic acid assays such as nucleic acid hybridization assays and assays which detect amplification of specific nucleic acid to detect for a nucleic acid sequence of the human MTT1 described herein.

Accepted means for conducting hybridization assays are known and general overviews of the technology can be had from a review of: *Nucleic Acid Hybridization. A Practical Approach* [72]; *Hybridization of Nucleic Acids Immobilized on Solid Supports* [41]; *Analytical Biochemistry* [4] and Innis et al., *PCR Protocols* [74], supra, all of which are incorporated by reference herein.

Target specific probes may be used in the nucleic acid hybridization diagnostic. The probes are specific for or complementary to the target of interest. For precise allelic differentiations, the probes should be about 14 nucleotides long and preferably about 20–30 nucleotides. For more general detection of the human MTT1 of the invention, nucleic acid probes are about 50 to about 1000 nucleotides, most preferably about 200 to about 400 nucleotides.

The specific nucleic acid probe can be RNA or DNA polynucleotide or oligonucleotide, or their analogs. The probes may be single or double stranded nucleotides., The probes of the invention may be synthesized enzymatically, using methods well known in the art (e.g., nick translation, primer extension, reverse transcription, the polymerase chain reaction, and others) or chemically (e.g., by methods such as the phosphoramidite method described by Beaucage and Carruthers [19], or by the triester method according to Matteucci, et al. [62], both incorporated herein by reference).

An alternative means for determining the presence of the human MTT1 is in situ hybridization, or more recently, in situ polymerase chain reaction. In situ PCR is described in Neuvo et al. [71], Intracellular localization of polymerase chain reaction (PCR)-amplified Hepatitis C cDNA; Bagasra et al. [10], Detection of Human Immunodeficiency virus type 1 provirus in mononuclear cells by in situ polymerase chain reaction; and Heniford et al. [35], Variation in cellular EGF receptor mRNA expression demonstrated by in situ reverse transcriptase polymerase chain reaction. In situ hybridization assays are well known and are generally described in *Methods Enzymol.* [67] incorporated by reference herein. In an in situ hybridization, cells are fixed to a solid support, typically a glass slide. The cells are then contacted with a hybridization solution at a moderate temperature to permit annealing of target-specific probes that are labelled. The probes are preferably labelled with radio-isotopes or fluorescent reporters.

The above described probes are also useful for in-situ hybridization or in order to locate tissues which express this gene, or for other hybridization assays for the presence of this gene or its mRNA in various biological tissues. In-situ hybridization is a sensitive localization method which is not dependent on expression of antigens or native vs. denatured conditions.

The inhibitory nucleic acids can be targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory nucleic acid complementary to regions of c-myc mRNA inhibits c-myc protein expression in a human promyelocytic leukemia cell line, HL60, which overexpresses the c-myc proto-oncogene. See Wickstrom E. L., et al. [93] and Harel-Bellan, A., et al. [31A]. As described in Helene and Toulme, inhibitory nucleic acids targeting mRNA have been shown to work by several different mechanisms to inhibit translation of the encoded protein(s).

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that affects either chemical, or enzymatic cleavage. Alternatively, cleavage can be induced by the use of ribozymes or catalytic RNA. In this approach, the inhibitory nucleic acids would comprise either naturally occurring RNA (ribozymes) or synthetic nucleic acids with catalytic activity.

Also, this invention provides an antisense molecule capable of specifically hybridizing with the isolated nucleic acid of the MTT1 gene. This invention provides an antagonist capable of blocking the expression of the peptide or polypeptide encoded by the isolated DNA molecule. In one embodiment the antagonist is capable of hybridizing with a double stranded DNA molecule. In another embodiment the antagonist is a triplex oligonucleotide capable of hybridizing to the DNA molecule. In another embodiment the triplex oligonucleotide is capable of binding to at least a portion of the isolated DNA molecule with a nucleotide sequence.

The antisense molecule may be DNA or RNA or variants thereof (i.e. DNA or RNA with a protein backbone). The present invention extends to the preparation of antisense nucleotides and ribozymes that may be used to interfere with the expression of the receptor recognition proteins at the translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. In the cell, they hybridize to that mRNA, forming a double stranded molecule. The cell does not translate an mRNA in this double-stranded form. Therefore, antisense nucleic acids interfere with the expression of mRNA into protein.

Antisense nucleotides or polynucleotide sequences are useful in preventing or diminishing the expression of the MTT1 gene, as will be appreciated by those skilled in the art. For example, polynucleotide vectors containing all or a portion of the MTT1 gene or other sequences from the MTT1 (particularly those flanking the MTT1 gene) may be placed under the control of a promoter in an antisense orientation and introduced into a cell. Expression of such an antisense construct within a cell will interfere with MTT1 transcription and/or translation and/or replication. Oligomers of about fifteen nucleotides and molecules that hybridize to the AUG initiation codon are particularly efficient. since they are easy to synthesize and are likely to pose fewer problems than larger molecules upon introduction to cells.

This invention provides a method of substantially inhibiting translation termination efficiency of mRNA and/or degradation of aberrant transcripts in a cell, said method comprising: a) providing a cell containing the DNA; b) overexpressing said DNA in said cell to produce an overexpressed polypeptide that binds to MTT1 and interferes with MTT1 function.

This invention provides a method of substantially inhibiting translation termination efficiency of mRNA and/or degradation of aberrant transcripts in a cell in a cell, said method comprising: a) providing a cell; b) expressing antisense transcript of the complex in sufficient amount to bind to the complex.

This invention provides a method of substantially inhibiting translation termination in a cell, said method comprising: mutating the complex comprising MTT1, Upf1p, Upf2p, Upf3p, eRF1, and eRF3, such that essentially no functional complex is produced in said cell.

This invention provides a method for treating a disease associated with translation termination efficiency of mRNA and/or degradation of aberrant transcripts, comprising administering to a subject administering to a subject a therapeutically effective amount of a pharmaceutical composition comprising the complex which is introduced into a cell of a subject; and a pharmaceutical carrier or diluent, thereby treating the subject.

In one embodiment, the invention provides a method of treating a patient having or at risk of having early stage as a result of genetic deficiency, disease or clinical treatment wherein the condition has an etiology associated with a defective, the method comprising administering to the patient a therapeutically effective amount of a formulation or composition which modulates the expression of the complex such that the state of the patient is ameliorated.

"Therapeutically effective" as used herein, refers to an amount formulation that is of sufficient quantity to ameliorate the state of the patient so treated. "Ameliorate" refers to a lessening of the detrimental effect of the disease state or disorder in the patient receiving the therapy. The subject of the invention is preferably a human, however, it can be envisioned that any animal can be treated in the method of the instant invention.

This has obvious implications for drug targeting, in that one or the other domain can be targeted for drug developement, e.g., using the combinatorial library techniques or rational drug design techniques.

In view of the foregoing, it becomes apparent that the present invention provides a number of routes for affecting fidelity of several aspects of translation fidelity, namely inhibition, elongation, and termination, which has important implications for antiviral therapy and for suppression of pathological nonsense mutations. Thus, the present invention provides drugs for use as antiviral compounds or to alter ribosomal decay.

The term "drugs" is used herein to refer to a compound or agents, such as an antibiotic or protein, that can affect function of the peptidyl transferase center during initiation, elongation, termination, mRNA degradation. Such compounds can increase or decrease aberrant mRNA and the efficiency of translation termination.

Gene Therapy and Transgenic Vectors

In one embodiment, a nucleic acid encoding the complex or factors of the complex; an antisense or ribozyme specific for the complex, or specific for regions of the release factors, MTT1, and Upf1p, are introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, adipose tissue can be specifically targeted. Examples of particular vectors include, but are not limited to, a defective herpes virus 1 (HSV1) vector [Kaplitt et al., *Molec. Cell. Neurosci.* 2:320–330 (1991)], an attenuated adenovirus vector, such as the vector described by Stratford-Perricaudet et al. [*J. Clin. Invest.* 90:626–630 (1992)], and a defective adeno-associated virus vector [Samulski et al., *J. Virol.* 61:3096–3101 (1987); Samulski et al., *J. Virol.* 63:3822–3828 (1989)].

In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, *J. Virol.* 62:1120; Temin et al., U.S. Pat. No. 5,124,263; International Patent Publication No. WO 95/07358, published Mar. 16, 1995, by Dougherty et al.; and Kuo et al., 1993, Blood 82:845. Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413–7417 (1987); see Mackey, et al., *Proc. Natl. Acad. Sci. U.S.A.* 85:8027–8031 (1988)]. The use of cationic lipids may promote encapsulation of negatively charged nucleic acids, and also promote fusion with negatively charged cell membranes [Felgner and Ringold, *Science* 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancrease, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990].

In a further embodiment, the present invention provides for co-expression of a gene product that modulates activity at the peptidyl transferase center and a therapeutic heterologous antisense or ribozyme gene under control of the specific DNA recognition sequence by providing a gene therapy expression vector comprising both a gene coding for a modulator of a peptidyl transferase center (including but not limited to a gene for a mutant frameshift or mRNA decay protein, or an antisense RNA or ribozyme specific for mRNA encoding such a protein) with a gene for an unrelated antisense nucleic acid or ribozyme under coordinated expression control. In one embodiment, these elements are provided on separate vectors; alternatively these elements may be provided in a single expression vector.

Antiviral Therapy

In yet a further embodiment, the present invention provides the means to treat viral infections by providing agents that modulate translation fidelity, and thus directly affect viral replication or assembly of viral particles.

The present invention advantageously provides drugs and methods to identify drugs for use in antiviral therapy of viruses that use the basic −1 ribosomal frameshifting mechanism, which includes four large families of animal viruses and three large families of plant viruses. Specifically, this invention provides assays for screening agents, antagonist/agonists, which effect frameshifting involving the complex, and which involve Upf3p. Also, this invention provides a mutant Upf3.

For example, almost all retroviruses use −1 ribosomal frameshifting, including lentiviruses (immunodeficiency viruses) such as HIV-1 and HIV-2, SIV, FIV, BIV, Visna virus, Arthritis-encephalitis virus, and equine infectious anemia virus; spumaviruses (the foamy viruses), such as human foamy virus and other mammalian foamy viruses; the T cell lymphotrophic viruses, such as HTLV-I, HTLV-II, STLVs, and BLV; avian leukosis viruses, such as leukemia and sarcoma viruses of many birds, including commercial poultry; type B retroviruses, including mouse mammary tumor virus; and type D retroviruses, such as Mason-Pfizer monkey virus and ovine pulmonary adenocarcinoma virus. In addition, many coronaviruses use the −1 frameshifting, including human coronaviruses, such as 229-E, OC43; animal coronaviruses, such as calf coronavirus, transmissible gastroenteritis virus of swine, hemagglutinating encephalomyelitis virus of swine, and porcine epidemic diarrhea virus; canine coronavirus; feline infectious peritonitis virus and feline enteric coronavirus; infectious bronchitis virus of fowl and turkey bluecomb virus; mouse hepatitis virus, rat coronavirus, and rabbit coronavirus. Similarly, torovirus (a type of coronavirus) is implicated, such as human toroviruses associated with enteric and respiratory diseases; breda virus of calves and bovine respiratory virus; berne virus of horses; porcine torovirus; feline torovirus. Another coronavirus is the arterivirus, which includes simian hemorrhagic fever virus, equine arteritis virus, Lelystad virus (swine), VR2332 virus (swine), and lactate dehydrogenase-elevating virus (rodents). Other animal viruses are paramyxoviruses, such as human −1 ribosomal frameshifting reported in measles, and astroviruses, such as human astroviruses 1–5, and bovine, ovine, porcine, canine, and duck astroviruses.

The plant viruses that involve a −1 frameshifting mechanism include tetraviruses, such as sobemoviruses (e.g., southern bean mosaic virus, cocksfoot mettle virus), leuteoviruses (e.g., barley yellowswarf virus, beet western yellows virus, and potato leaf roll virus), enamoviruses (e.g., pea mosaic virus), and umbraviruses (e.g., carrot mottle virus); tombusviruses, such as tombusvirus (e.g., tomato bushy stunt virus), carmovirus (e.g., carnation mottle virus), necrovirus (e.g., tobacco necrosis virus); dianthoviruses (e.g., red clover necrotic mosaic virus), and machiomovirus (e.g., maize chlorotic mottle virus).

In addition, totiviruses, such as L-A and L-BC (yeast) and other fungal viruses, giradia lamblia virus (intestinal parasite), triconella vaginell virus (human parasite), leishmania brasiliensis virus (human parasite), and other protozoan viruses are −1 frameshift viruses.

According to the invention, the component or components of a therapeutic composition of the invention may be introduced or administered parenterally, paracancerally, transmucosally, transdermally, intramuscularly, intravenously, intradermaly, subcutaneously, intraperitonealy, intraventricularly, or intracranialy.

Modes of delivery include but are not limited to: naked DNA, protein, peptide, or within a viral vector, or within a liposome. In one embodiment the viral vector is a retrovirus, adeno-associated virus, or adenovirus.

As can be readily appreciated by one of ordinary skill in the art, the compositions and methods of the present invention are particularly suited to treatment of any animal, particularly a mammal, more specifically human. But by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

As used herein, "pharmaceutical composition" could mean therapeutically effective amounts of the complex with suitable diluents, preservatives, solubilizers, emulsifiers, adjuvants and/or carriers useful in SCF therapy. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of SCF. The choice of compositions will depend on the physical and chemical properties of the protein having SCF activity. For example, a product derived from a membrane-bound form of SCF may require a formulation containing detergent. Controlled or sustained release compositions include formulation in lipophilic depots (e.g., fatty acids, waxes, oils). Also comprehended by the invention are particulate compositions coated with polymers (e.g., poloxamers or poloxamines) and SCF coupled to antibodies directed against tissue-specific receptors, ligands or antigens or coupled to ligands of tissue-specific receptors.

Other embodiments of the compositions of the invention incorporate particulate forms protective coatings, protease inhibitors or permeation enhancers for various routes of administration, including parenteral, pulmonary, nasal and oral.

Further, as used herein "pharmaceutically acceptable carrier" are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. As is appreciated by those skilled in the art the amount of the compound may vary depending on its specific activity and suitable dosage amounts may range from about 0.1 to 20, preferably about 0.5 to about 10, and more preferably one to several, milligrams of active ingredient per kilogram body weight of individual per day and depend on the route of administration. In one embodiment the amount is in the range of 10 picograms per kg to 20 milligrams per kg. In another embodiment the amount is 10 picograms per kg to 2 milligrams per kg. In another embodiment the amount is 2–80 micrograms per kilogram. In another embodiment the amount is 5–20 micrograms per kg.

The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

In yet another embodiment, the therapeutic compound can be delivered in a controlled release system. For example, the complex may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)). Preferably, a controlled release device is introduced into a subject in proximity of the site of inappropriate immune activation or a tumor. Other controlled release systems are discussed in the review by Langer (Science 249:1527–1533 (1990)).

As can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

EXPERIMENTAL DETAILS SECTION

EXAMPLE 1

A Family of RNA Helicases are Modulators of Translation Termination

Materials and Methods

General yeast methods: Yeast Media, transformations, RNA isolation, blotting and hybridization were as described (Rose et al., 1990, Weng et al. 1996a, Hagan et al. 1995, Scheistl and Geitz 1989).

Preparation of glutathione Sepharose-RF fusion complexes and of purifed RF-fusion proteins: The glutathione sepharose-RF fusion complexes were prepared as described previously (Czaplinski et al., 1998). 1 $\mu$l of GST-RF complexes typically contained 0.9 $\mu$g GST-eRF1 or 1.5 $\mu$g GST-eRF3, while GST complexes typically contained 4.5 $\mu$g GST per $\mu$l of resin. Purified GST-RF's were also prepared from cultures of BL21(DE3) pLysS cells transformed with pGEX2T, pGEX2T-SUP35 or pGEX2T-SUP45 and the fusion proteins were isolated as described previously (Czaplinski et al., 1998).

Preparation of cytoplasmic extracts: BJ3505 (MATαpep4::HIS3 prb-Δ1.6R HIS3 lys2–208 trp1-Δ10 ura3–52 gal2 can1) cells were grown to an $OD_{600}$=1.0 and washed in 5 ml of cold Buffer IB (IBTB lacking BSA) with 0.5 mM PMSF. Cells were repelleted and suspended in 1.3 ml of cold IB with 0.5 mM PMSF and protease inhibitors (PI, 1 $\mu$g/ml each Leupeptin, Aprotinin and pepstatin A) per g of cell weight. An approximately equal volume of glass beads was added and lysis was achieved by vortexing 6 times for 20 seconds, with 1 minute cooling on ice in between vortexing. The lysate was removed, and the beads washed 2 times with an equal volume of IB with 0.5 mM PMSF and 1 $\mu$g/ml each Leupeptin, Aprotinin and pepstatin A. The washes were combined with the lysate and the cell debris was removed by centrifugation at 30,000×g for 20 min.

ATPase assays: Mtt1p RNA-dependent ATPase activity was determined using 20 ng Mtt1p in the presence of GST-RF fusion proteins by a charcoal assay as described previously (Czaplinski et al. 1995) using 1 $\mu$g/ml poly(U) RNA with and 100 $\mu$g/ml BSA. The results are plotted as pmol of $^{32}$P released versus the concentration of the indicated protein.

Results

Figure 2:
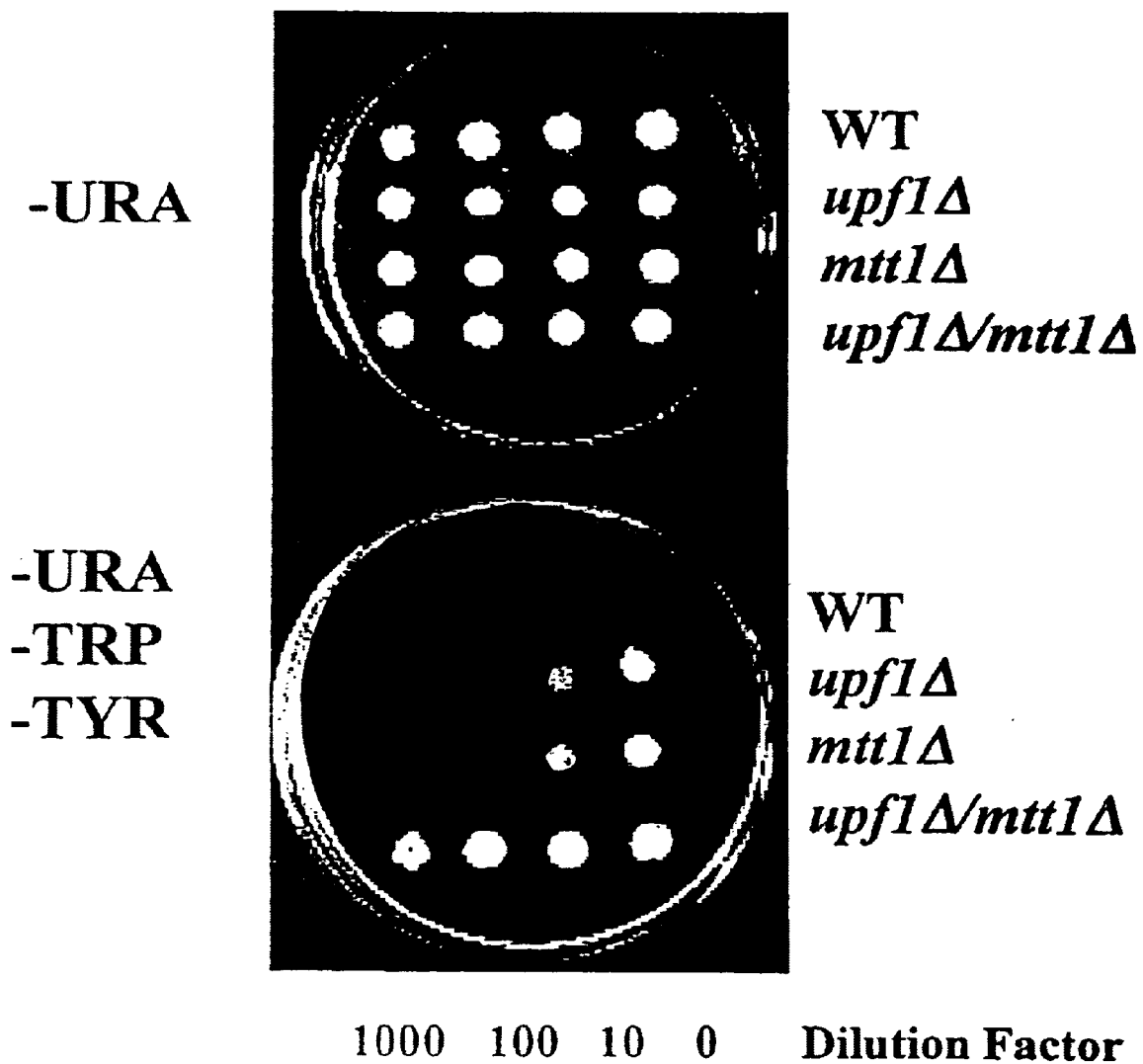
FIG. 2 An mtt1Δ demonstrates nonsense suppression. MTT1, UPF1, or MTT1 and UPF1 were deleted from yeast strain KC2 (ura3-52 trp1D leu2-2 tyr7-1) and these cells were grown to $OD_{600}$=1.0. Serial dilutions of these cells were plated on -ura-leu-tyr to assay for nonsense suppression, and -ura as a control for cell growth. Growth was monitored at 30° C. and 10 days growth is pictured above.

Identification of a family of yeast superfamily group I helicases that are similar to the UPF1 gene: A sequence comparison to identify other yeast genes that are homologous to the UPF1 was undertaken and the results are shown in FIG. 1. The SEN1 gene demonstrated significant homology with UPF1 (FIG. 2; see Koonin, 1992). SEN1 was identified in a screen for mutations that affect tRNA splicing and harbors all of the motifs to be considered a superfamily group I helicase (Winey and Culbertson, 1988, DeMarini et al. 1992). The previously identified DNA2 gene also demonstrated significant homology to UPF1 (FIG. 2). DNA2 is likely to have a role in DNA replication, possibly in processing Okazaki fragments (Budd et al. 1995, Budd and Campbell 1997). Two additional genes encoding superfamily group I helicases with high homology to UPF1 were also identified and in previous studies have been named Helicase A (HCSA, Biswas et al. 1997a,b) and Helicase B (HCSB, Biswas et al. 1995) or scHel1 (Bean and Matson, 1993). For reasons that will be described below, the gene encoding Helicase B (HCSB), is named MTT1 (for Modulator of Translation Termination). The proteins encoded by the HCSA and MMT1 genes have been previously purified and demonstrated to have DNA-dependent helicase activity (Biswas et al., 1995; Biswas et al., 1997a,b; Bean and Matson, 1993). HCSA and HCSB have been suggested to be involved in chromosome replication (Biswas et al., 1995, 1997a,b). This notion is based on the observations that; 1) the yeast single-stranded DNA binding protein Rpa1p enhances their DNA helicase activities (Biswas et al., 1995, 1997) and 2) HcsA co-purified with DNA polymerase α, and displays the biochemical properties of replicative helicases (Biswas et al., 1997a,b). To date there is no in vivo evidence that suggests the involvement of HCSA or HCSB in replication. Both hcsaΔ and hcsbΔ strains are viable. hcsbΔ strains do not display defects in growth, sensitivity to DNA damage, or respiratory defects (Bean and Matson, 1997). Transposon insertion into the promoter region of MTT1 has been reported to cause hypersensitivity to calcofluor white, a cell wall synthesis inhibitor and hygromycin B, a drug which induces translational misreading (Lussier et al. 1997). Homology of HcsA and HcsB has been noted previously (Biswas et al. 1997a). The homology among these five yeast helicases appears to be confined to their helicase domains (FIG. 2).

Eight conserved motifs are associated with all superfamily group I helicases (Gorbalenya, 1988, Koonin, 1992). Within these eight motifs, a limited number of residues is conserved among all superfamily group I helicases. Although these 8 motifs are spaced variably from protein to protein, according to the crystal structure of 2 different superfamily group I helicases, these conserved residues are all in close proximity in 3 dimensions (2 crystal structure papers). A more careful analysis of the genes with similarity to UPF1 identifies this group as a subclass of superfamily group I which, the UPF1-like subclass. The distinguishing feature of this subclass is a more extensive homology surrounding the conserved residues in motifs II, IV, V and VI (FIG. 2) which has been noted previously (Perlick et al. 1996). Furthermore two additional motifs within this domain are conserved among these five genes. The first is located between motifs III and IV (consensus lexSLFervl, (SEQ ID NO:10) FIG. 2) and the second is located between motifs IV and V (consensus IgvitpYxaQ; (SEQ ID NO:11) FIG. 2), refered as motif IIIa and IVa, respectively. These additional motifs are present in the human homolog of the Upf1gene as well. Of these five yeast genes, Dna2p is the poorest fit to the consensus, and omission of this sequence yields a tighter consensus. Two other superfamily group I helicases from yeast, Pif1 and RadH, and two well characterized group I helicases from *E. coli*, Rep and uvrD, could not be aligned to these five sequences under these parameters, indicating that the homology is not general to all superfamily group I helicases, thus evidence for a distinct subclass.

As described above, a unique feature of the Upf1p is that it contains a cysteine-histidine-rich region near it amino terminus (FIG. 2C). Mutations in this region have been shown to reduce translation termination efficiencies at nonsense codons and enhance programmed -1 ribosomal frameshifting efficiencies (Weng et al., 1996b; Cui et al., 1996). This region has been identified as the Upf2 interaction domain (Weng et al, 1996b, He et al. 1996). Interestingly, the Mtt1 p also contains a cysteine-histidine rich region near its amino terminus (Bean and Matson, 1997). Within the first 127 amino acids, 13 cysteines and 3 histidines are present. Although the cysteine-histidine rich regions of UPF1 and MTT1 contain no apparent homology, both regions have the potential to form ring fingers (see Weng et al., 1996b, Bean and Matson, 1997). Furthermore these regions can be matched to multiple zinc-binding motifs. However, due to the considerable number of cysteine residues, any alignment of this type leaves several cysteine residues unaccounted for within the same region.

A mtt1Δ strain demonstrates a nonsense suppression phenotype:. Nonsense suppression results when a near cognate tRNA successfully competes with the termination factors at a nonsense mutation so that amino acid incorporation into the peptide chain occurs rather than prematurely terminating translation (FIG. 1). Sufficient levels of nonsense suppression allows production of completed polypeptide protein which can support growth. A upf1Δ strain allows nonsense suppression of these alleles. Based on these observations, it was determined that Mtt1p is involved in modulating translation termination at a stop codon. To test this possibility, wild-type, mtt1Δ, upf1Δ, upf1Δ mtt1Δ strains harboring leu2-2 and tyr7-1 nonsense alleles were assayed for suppression of these alleles. The suppression phenotype of strains harboring the leu2-2 and tyr7-1 nonsense alleles was monitored by plating cells on -trp-leu-tyr media. As a control, these cells were plated on -trp media. The results demonstrated that the both upf1Δ and mtt1Δ cells harboring grew on both types of media (FIG. 3A), indicating that deleting either the UPF1 or MTT1 genes allowed suppression of the tyr7-1 and leu2-1 nonsense alleles (FIG. 3A). Wild-type (UPF1$^+$ MTT1$^+$) cells were unable to grow on -trp-leu-tyr media, demonstrating that the presence of these genes prevented suppression of these nonsense alleles (FIG. 3A).

The nonsense suppression phenotype of a upf1Δ mtt1Δ strain was also monitored as described above and compared to strains harboring single deletions. The results from these experiments demonstrated that a upf1Δ mtt1Δ strain was much more effective in suppressing the tyr7-1 and leu2-1 nonsense alleles than strains harboring single deletions of either the UPF1 or MTT1 gene (FIG. 3A). Taken together, these results demonstrate that both the Upf1p and Mtt1p is involved in modulating translation termination at nonsense codons.

Previous results demonstrated that a upf1Δ strain was also able to enhance frameshift suppression at 37° C. in strains harboring the his4–38 allele and a SUF1 tRNA frameshift suppressor while strains harboring the wild-type UPF1 gene could not grow at this temperature (Leeds et al., 1991, 1992). It was shown that a mtt1Δ his4–38 SUF1 strain would also be able to enhance frameshift suppression. The results demonstrated that, unlike a upf1Δ strain, mtt1Δ his4–38

SUF1 strain was unable grow on media lacking histidine at 37° C., indicating that deleting the MTT1 gene did not increase frameshift suppression in this assay.

A mtt1Δ strain does not affect nonsense-mediated mRNA decay: Previous results demonstrated that the Upf1p has a role in regulating both mRNA turnover and translation termination (Weng et al. 1996a,b, 1998; Czaplinski et al., 1998). Based on these results, it was determined whether the nonsense suppression phenotype observed above was a consequence of affecting the efficiency of translation termination, inactivating the nonsense-mediated mRNA decay pathway (NMD), or a combination of affecting the two pathways. A mtt1Δ strain harboring the tyr7-1 and keu2-2 nonsense containing alleles was constructed to ask this question (see Experimental Procedures). A mtt1Δ strain was shown to be viable with no demonstrable growth defects (See Experimental Procedures). The effect of a mtt1Δ on NMD was examined by monitoring the abundance of the CYH2 precursor and mature mRNA, which encodes a ribosomal protein. The inefficiently spliced CYH2 precursor, which contains an intron near the 5' end, is a naturally occurring substrate for the nonsense-mediated mRNA decay (NMD) pathway (He et al., 1993). The abundance of the nonsense-containing tyr7 and leu2 transcripts was also determined in these strains. The results demonstrated that the steady-state levels of CYH2 precursor and mature mRNA, the tyr7 and leu2 mRNAs were equivalent to that found in a wild-type strain (FIG. 3). As a control, the CYH2 precursor and nonsense-containing tyr7 and leu2 transcripts were increased in a upf1Δ strain. The abundance of the wild-type CYH2 transcript, which is not a substrate of the NMD pathway, was equivalent in all strains tested (FIG. 3). Furthermore, the abundance of the transcripts that are substrates for the NMD pathway are not affected any greater in a upf1Δ mtt1Δ strain versus only a upf1Δ strain (FIG. 3). A upf1Δ mtt1Δ strain was viable with no discernable growth defects.

Figure 5:
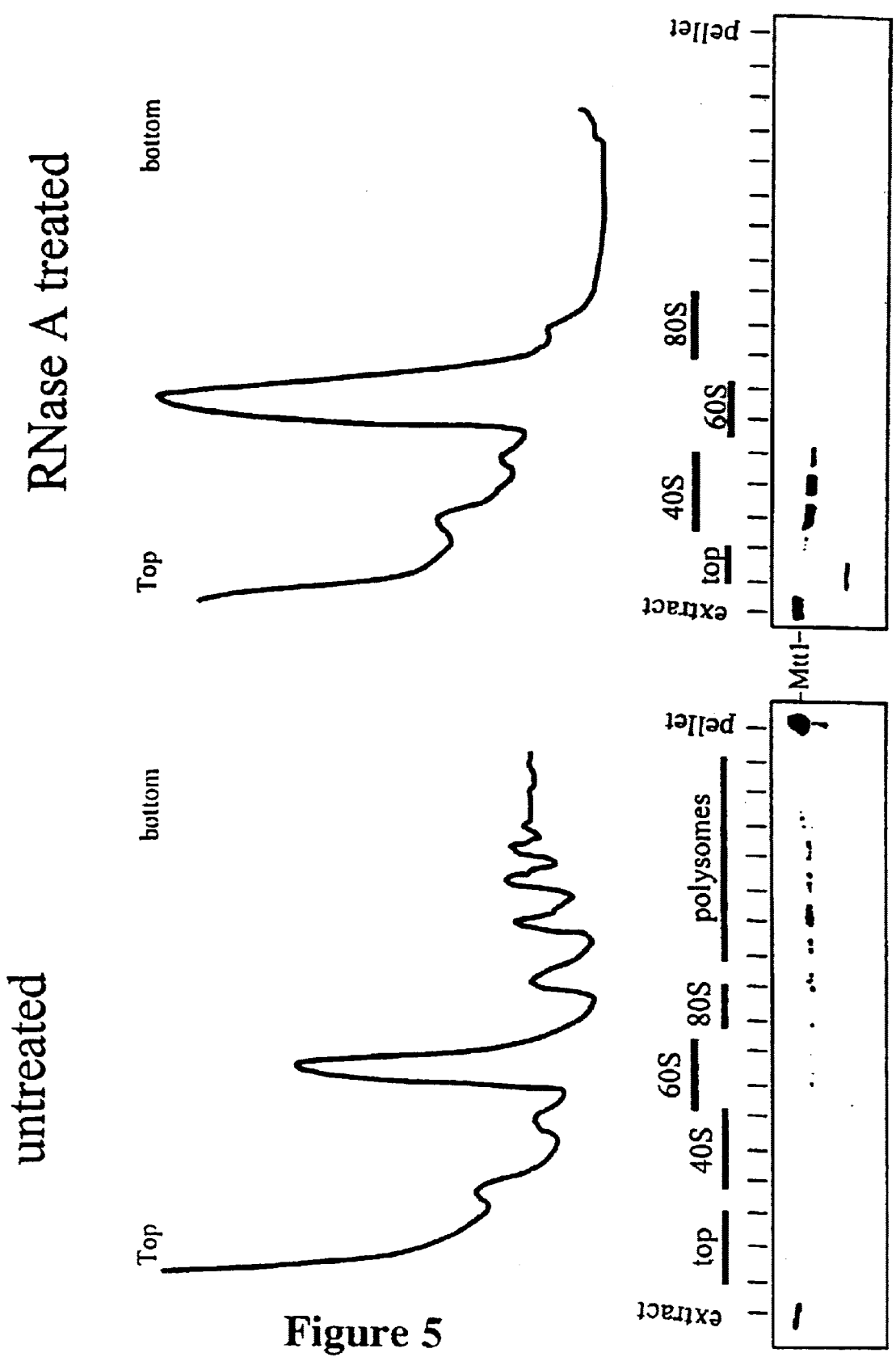
FIG. 5 Mtt1 is polysome associated. Cytoplasmic extracts from a yeast strain BJ3505 transformed with pG-1FLAGMTT1 were prepared and either treated with RNAse A or left untreated. Extracts were then centrifuged through a 7–47% sucrose gradient. Gradients were harvested and fractions were collected while monitoring $A_{254}$. Gradient fractions were subjected to western blotting using monoclonal antibody to the Flag epitope as a probe. $A_{254}$ profiles are shown in the top panels while western blots of the corresponding fractions are shown in the bottom panels.

The Mtt1p interacts with the peptidyl release factor eRF3: Previous results suggested that the Upf1p affects translation termination by directly interacting with the translation termination factors eRF1 and eRF3 and therefore may affect their efficiency of translation termination (Czaplinski et al., 1998). Since deleting the MTT1 gene also promotes nonsense suppression of the tyr7-1 and leu2-2 alleles, Mtt1p also interacts with the peptidyl release factors. To test this, eRF1 and eRF3 were individually expressed in *E. coli* as glutathione-S-transferase (GST) fusion proteins and purified using glutathione sepharose beads. The purified GST-RF (release factor) fusion proteins associated with the glutathione sepharose beads were added to a yeast cytoplasmic extract containing a FLAG epitope-tagged Mtt1p (see Experimental Procedures). Following incubation, the GST-RFs and associated proteins were purified by affinity chromatography and subjected to SDS-PAGE. Immunoblotting was performed and the presence of the Flag-Mtt1p was assayed using an antibody against the FLAG epitope. The anti-FLAG antibody recognized only the 127 kD Mtt1p in cytoplasmic extracts from cells transformed with plasmid expressing the FLAG-Upf1p. This analysis also demonstrated that the Mtt1p specifically co-purified with eRF3 (FIG. 5). Mtt1p did not co-purify with either GST-RF1 or GST protein that was not fused to another protein (FIG. 5) or a GST-JIP protein, in which a Jak2 interacting protein fused to GST was used to monitor the specificity of the reaction.

The Mtt1p is polysome-associated: Based on nonsense suppression phenotypes of a mtt1Δ strain, it was investigated whether the Mtt1p is associated with ribosomes. To determine whether the Mtt1p is ribosome-associated, post-mitochondrial extracts were prepared from cells harboring the Flag-Mtt1 gene and the polysome fractions were separated by centrifugation through sucrose gradients. The various fractions were collected and the presence of the Flag-Mtt1p protein in the gradient fractions were determined by Western blotting, probing the blots with an antibody directed against the Flag epitope. The results from these experiments indicated that the Flag-Mtt1p is polysome- and monosome-associated while the upper fractions contained no detectable Mtt1p (FIG. 6 lanes 2 and 3). The Mtt1p associated with the polysome fraction consists predominantly of an 127 kD protein. Treatment of the polysome extracts with RNase A shifted the Mtt1p to fractions which contain the 40 S subunits.

The Mtt1p demonstrates RNA-dependent ATPase and helicase activities: Previous results have shown that Mtt1p has DNA-dependent ATPase and helicase activities (Biswas et al., 1995). Based on the results described above, it was shown that Mtt1p also will be an RNA-dependent ATPase and helicase. It was first asked whether purified Mtt1p exhibited ATPase activity. ATPase assays were performed by incubating the purified protein in reaction mixtures containing radiolabelled [$\gamma$-$^{32}$P]ATP in the presence or absence of a poly-uridine (poly(rU)) and assaying the release of $^{32}$PO$_4$. The results demonstrated that in the absence of poly(rU) no ATPase activity was detectable (FIGS. 7). Reaction mixtures containing poly(rU), however, greatly stimulated the release of $^{32}$PO$_4$, indicating that Mtt1p also harbored an RNA-dependent ATPase activity (FIG. 7). Concentrations of poly(rU) at or above 330 nM maximally stimulated the ATPase activity of the Upf1p.

Discussion

The results presented here describe the identification of Mtt1p, a nucleic acid dependent helicase with significant homology to the Upf1p, a factor previously identified in regulating both translation termination and NMD (Czaplinski et al., 1995,1998; Weng et al., 1996a,b, 1998). Several lines of evidence indicate that Mtt1p also has a role in modulating the translation termination process. Interestingly, comparison of the MTT1 gene with other superfamily group I helicases identified unique signature motifs that tag this subfamily of superfamily group I helicases as possibly being involved in either RNA dependent or RNA-DNA dependent processes (FIG. 2). As will be discussed below, these results suggest that a subset of the Upf1p family of RNA helicases are involved in modulating the efficiency of the translation termination process.

The MTT1 gene and its protein product demonstrate similarity to the Upf1p: A comparison of the MTT1 and UPF1 genes identified several regions of similarity. Both proteins contain a cysteine-histidine rich region near the amino terminal end of the protein and harbor all of the motifs to be a superfamily group I helicase (FIG. 2). The cysteine-histidine rich regions of UPF1 and MTT1 are not very homologous. It is also conceivable that these cysteine-histidine-rich regions form a new type of cysteine-histidine-rich motif. Interestingly, mutations in the cysteine-histidine rich region of UPF1 have been shown previously to increase programmed −1 frameshifting efficiencies and promote nonsense suppression (Cui et al., 1996; Weng et al., 1996b).

Sequence comparisons of superfamily group I helicases initially identified SEN1 and MOV-10 genes as having strong regions of homology to the UPF1 gene helicase region (Koonin, 1992). MTT1 gene also demonstrates extensive homology to UPF1 and to other members of the UPF1-like subfamily (FIG. 2). These genes include DNA2, HCSA, HCSB/MTT1, and SEN1. In particular, another member of the UPF1 family of helicases is the recently isolated HelB gene (Biswas et al., 1997a,b). This helicase was initially isolated as part of the multienzyme polymerase a complex (Biswas et al., 1993,1993a,1995). Deletion of HCSA does not cause nonsense suppression, demonstrating that the nonsense suppression phenotypes observed in upf1Δ and mtt1Δ strains are not simply due to deleting a group I helicase.

The Mttp1p is an RNA helicase involved in translation termination: Previous results demonstrated that the Hel1p/Mtt1p demonstrated DNA helicase activity that was stimulated by the yeast single-stranded DNA binding protein Rpalp (Biswas et al., 1995; Bean and Matson, 1997). The results presented here demonstrated that the purified Mtt1p also shows RNA-dependent ATPase and helicase activities (FIG. 7). Thus, similar to Upf1p (Czaplinski et al., 1995), Mtt1p also demonstrates the ability to unwind both DNA and RNA duplexes.

Several lines of evidence suggest that Mtt1p is involved in translation termination The results presented here show that; 1) a mtt1Δ strain demonstrates a nonsense suppression phenotype (FIG. 4); 2) the Mtt1p is polysome associated (FIG. 6); 3) the Mtt1p directly interacts with the peptidyl release factor eRF3 (FIG. 5); 4) mtt1Δ strains demonstrate paromomycin sensitivity. If one considers that, unlike a upf1Δ strain, a mtt1Δ strain does not stabilize nonsense-containing transcripts, then the amount of nonsense suppression per RNA molecule is greater in a mtt1Δ strain than in a upf1Δ strain (FIG. 3).

A mtt1Δ upf1Δ strain demonstrates a dramatic nonsense suppression phenotype compared with a upf1Δ or mtt1Δ strain. One possibility to explain this observation is that these proteins function at the same step in translation termination and that either Mtt1p or Upf1p can partially compensate for the loss of the other factor. Inactivation of both factors, however, leads to a much higher level of nonsense suppression. An Alternative explanation is that these two factors work at different steps in the termination process. Both Mtt1p and Upf1p function in modulating the efficiency of translation termination and Upf1p acts subsequently in promoting decay of the mRNA. The synergistic increase in nonsense suppression may be a consequence of both increasing the amount of the nonsense-containing transcript and reducing the efficiency of translation termination in a mtt1Δ upf1Δ strain.

At least two RNA helicases are involved in modulating the efficiency of translation termination: It is interesting that there appears to be at least two helicases involved in modulating the efficiency of translation termination. Helicases are enzymes that unwind a nucleic acid duplexes. It has now become clear that the ability to manipulate nucleic acid duplexes by helicases is critical for every biological process in which DNA and RNA is involved. A large number of RNA helicases have been shown to be involved in post-transcriptional control mechanisms. Examples include tRNA processing, ribosomal biogenesis, splicing, transport, translation, and mRNA turnover. These RNA helicases fall into at least two families, the most prominent superfamily is the "DEAD box" helicases or superfamily group II. The superfamily group I helicases, as those shown in FIG. 2, have been shown unwind both DNA and RNA duplexes.

At present, it is not known or understood how Upf1p and Mtt1p modulate the translation termination process. The efficiency of translation termination can be affected by altering 1) the association rates of the eRFs with the ribosome, 2) the efficiency of the eRFs in promoting peptidyl hydrolysis, or 3) the rate of disassociation of the eRFs from the ribosome after translation termination has been completed. Assays to monitor these steps in the translation termination process in order to begin to understand at what step these proteins function.

The results presented here indicate that, although the translation machinery is highly precise, the growth rates of cells do not change under conditions that reduce the accuracy of this process. For example, a mtt1Δ upf1Δ strain did not demonstrate any affects on cell growth even though translation termination is less efficient in these cells. Furthermore, strains harboring the mof4-1 allele of UPF1 or a upf3Δ, which demonstrate four-fold increased programmed frameshifting efficiency and indicating a reduction of fidelity in the process of translation elongation, also do not show any growth defects (Cui et al., 1996; Ruiz-Echevarria et al., 1998).

REFERENCES

All-Robyn J. A., Kelley-Geraghty D., Griffin E., Brown, N., Liebman, S. W. 1990. Isolation of omnipotent suppressors in an [eta+] yeast strain. *Genetics* 124:505–514.

Altamura, N., Groudinsky, O., Dujardin, G. and Slonimski, P. P. (1992) NAM7 nuclear gene encodes a novel member of a family of helicases with a Z1-6n-ligand motif and is involved in mitochondrial functions in *Saccharomyces cerevisiae*. *J. Mol. Biol.* 224, 575–587.

Applequist, S. E., Selg, M., Roman C., and Jack, H. M. (1997) Cloning and characterization of HUPF1, a human homologue of the *Saccharomyces cerevisiae* nonsense mRNA-reducing UPF1 protein. *Nucleic Acids Res.* 25, 814–821.

Atkin A. L., Altamura, N. Leeds, P., and Culbertson, M. R. (1995) The majority of yeast UPF1 co-localizes with polyribosomes in the cytoplasm. *Mol. Biol. Cell* 6, 611–625.

Atkin, A. L., Schenkman, L. R., Eastham, M., Dahlseid, J. N., Lelivelt, M. J., Culbertson, M. R. (1997) Relationship between yeast polyribosomes and Upf1 proteins required for nonsense mediated mRNA decay. *J. Biol. Chem.* 272, 22163–22172.

Bean D. W. and Matson, S. W. 1997. Identification of the gene encoding scHeII, a DNA helicase from *Saccharomyces cerevisiae*. Yeast 13:1465–1475.

Bean D. W. Kallam, W. E. and Matson, S. W. 1993. Purification and characterization of a DNA helicase from *Saccharomyces cerevisiae*. J Biol Chem 268:21783–21790.

Bedwell DM, Kaenjak A, Benos DJ, Bebok Z, Bubien JK, Hong J, Tousson A, Clancy JP, Sorscher EJ. 1997. Suppression of a CFTR premature stop mutation in a bronchial epithelial cell line. Nature Med 1997 3:1280–1284.

Biswas, E. E., Fricke, W. M., Chen, P. H., Biswas, S. B. 1997a. Yeast DNA helicase A: cloning, expression, purification, and enzymatic characterization. Biochemistry. 36:13277–13284.

Biswas, S. B., Chen, P. H., and Biswas, E. E. 1997b. Purification and characterization of DNA polymerase α-associated replication protein A-dependent yeast DNA helicase A. Biochemistry 36 13270–13276.

Biswas, E. E., Chen, P. H., Leszyk, J., and Biswas, S. B. 1995. Biochemical and genetic characterization of a replication protein A dependent DNA helicase from the yeast, *Saccharomyces cerevisiae*. Biochem Biophys Res Commun 206:850–856.

Biswas, E. E., Chen, P. H. and Biswas, S. B. 1993a. DNA helicase associated with DNA polymerase alpha: isolation by a modified immunoaffinity chromatography. Biochemistry 32:13393–13398.

Biswas, E. E., Ewing, C. M. and Biswas, S. B. 1993b. Characterization of the DNA-dependent ATPase and a DNA unwinding activity associated with the yeast DNA polymerase alpha complex. Biochemistry. 2:3020–3026.

Buckingham, R., Grentzmann, G., and Kisselev, L. (1997) Polypeptide chain release factors. Mol. Microbiol. 24, 449–456.

Budd, M. E., Choe, W. C., and Campbell, J. L. 1995. DNA2 encodes a DNA helicase essential for replication of eukaryotic chromosomes. J. Biol. Chem. 270 26766–26769.

Budd, M. E., and Carnpbell, J. L. 1997. A yeast replicative helicase, Dna2, interacts with yeast FEN-1 nuclease in carrying out its essential function. Mol. Cell Biol. 17, 2136–42.

Cui, Y., Hagan, K. W., Zhang S., and Peltz, S. W. (1995) Identification and characterization of genes that are required for the accelerated degradation of mRNAs containing a premature translational termination codon. Genes & Dev. 9, 423–436.

Cui, Y., Dinman, J. D., and Peltz, S. W. (1996) mof4-1 is an allele of the UPF1/IFS2 gene which affects both mRNA turnover and −1 ribosomal frameshifting efficiency. EMBO J. 15, 5726–5736.

Czaplinski, K., Weng, Y., Hagan, K. W. and Peltz, S. W. (1995) Purification and characterization of the Upf1p: a factor involved in translation and mRNA degradation. RNA 1, 610–623.

Czaplinski, K., Ruiz-Echevarria, Weng, Y., Paushkin, S. V., Dietz, H., Ter-Avanesyan, M. D. and Peltz, S. W. 1998. Assembly of the mRNA surveillance complex occurs at a translation termination event. Genes & /Dev. In press DeMarini, D. J., Winey, M., Ursic, D., Webb, F. and Culbertson, M. R. 1992. SEN1, a positive effector of tRNA-splicing endonuclease in Saccharomyces cerevisiae. Mol Cell Biol 12:2154–2164.

Didichenko, S. A., Ter-Avanesyan, M. D., and Smirnov, V. N. (1991) EF-1a-like ribosome-bound protein of yeast Saccharomyces cerevisiae. Eur. J. Biochem. 198, 70.5–711.

Dinman, J. D., Ruiz-Echevarria, M. J. and Peltz, S. W. 1998. Translating old drugs into new treatments: Identifying compounds that modulate programmed −1 ribosomal frameshifting and function as potential antiviral agents. Trends in Biotech. 16:190–196.

Dinman, J. D. Ruiz-Echevarria, M. J., Czaplinski, K. and Peltz, S. W. 1997. Peptidyl-transferase inhibitors have antiviral properties by altering programmed −1 ribosomal frameshifting efficiencies: Development of model systems P.N.A.S. 94:6606–6611.

Frolova, L., Le Goff, X., Rasmussen, H. H., Cheperegin, S.,Drugeon, G., Kress, M., Arman, I., Haenni, A. L., Celis, L. E., Phillippe, M., Justesen, J., and Kisselev, L. (1994) A highly conserved eukaryotic protein family possessing properties of a polypeptide chain release factor. Nature 372, 701–703.

Frolova, L., Le Goff X., Zhouravleva, G., Davydova, E., Philippe, M. and Kisselev, L. (1996) Eukaryotic polypeptide chain release factor eRF3 is an eRF1- and ribosome-dependent guanosine triphosphatase. RNA 4, 334–341.

Gorbalenya AE, Koonin EV, Dochenko AP, Blinov VM. 1988. A novel superfamily of nucleoside triphosphate-binding motif containing proteins which are probably involved in duplex unwinding in DNA and RNA replication and recombination. FEBS Lett 235(1,2): 16–24.

Hagan, K. W., Ruiz-Echevarria, M. J., Quan, Y. and Peltz S. W. (1995) Characterization of cis-acting sequences and decay intermediates involved in nonsense-mediated mRNA turnover. Mol. Cell. Biol. 15, 809–823.

He, F., Brown, A. H., and Jacobson, A. (1997) Upf1p, Nmd2p, and Upf3p are interacting components of the yeast nonsense-mediated mRNA decay pathway. Mol. Cell. Biol. 17, 1580–94.

He, F., Peltz, S. W., Donahue, J. L., Rosbash, M. and Jacobson, A. (1993) Stabilization and ribosome association of unspliced pre-mRNAs in a yeast upf1-mutant. Proc. Natl. Acad. Sci. USA 90, 7034–7038.

Howard, M., Frizzell R. A. and Bedwell D. M. (1996) Aminoglycoside antibiotics restore CFTR function by overcoming premature stop mutations. Nature Med. 2,467–9.

Jacobson, A. and Peltz, S. W. (1996) Interrelationships of the pathways of mRNA decay and translation in eukaryotic cells. Ann. Rev. Biochem. 65, 693–739.

Koonin, E. V. (1992). A new group of putative RNA helicases. TIBS 17, 495–497.

Korolev, S. Hsieh, J., Gauss, G. H., Lohman, T. M. and Waksman, G. 1997. Major domain swiveling revealed by the crystal structures of complexes of E. coli Rep helicase bound to single-stranded DNA and ADP. Cell. 90:635–647.

Leeds, P., Peltz, S. W., Jacobson, A. and Culbertson, M. R. (1991) The product of the yeast UPF1 gene is required for rapid turnover of mRNAs containing a premature translational termination codon. Genes & Dev. 5, 2303–2314.

Leeds, P., Wood, J. M., Lee, B. S. and Culbertson, M. R. (1992) Gene products that promote mRNA turnover in Saccharomyces cerevisiae. Mol. Cell. Biol. 12, 2165–2177.

Lussier, M, White, A-M., Sheraton, J., di Paolo, T., Treadwell, J., Southard, S. B., Horenstein, C. I., Chen-Weiner, J., Ram, A. F. J., Kapteyn, J. C., Roemer, T. W., Vo, D. H., Bondoc, D. C., Hall, J., Zhong, W. W., Sdicu, A-M., Davies, J., Klis, F. M., Robbins, P. W., and Bussey, H. 1997. Large Scale identification of Genes Involved in Cell Surface Biosynthesis and Architecture in Saccharomyces cerevisiae. Genetics 147 435–450.

McKusick, V. A.; (with the assistance of Francomano, C. A., Antonarakis, S. E., and Pearson, P. L. (1994) Mendelian inheritance in man: a catalog of human genes and genetic disorders Johns Hopkins University Press. Baltimore MD. (Web site-http://www.ncbi.nlm.nih.gov/Omim/).

Palmer,E., Wilhelm,J. and Sherman,F. (1979) Phenotypic suppression of nonsense mutants in yeast by aminoglycoside antibiotics. Nature 277, 148–150.

Paushkin S. V., Kushnirov, V. V., Smimov, V. N. and Ter-Avanesyan, M. D. (1997a). In Vitro propagation of the prion-like state of yeast Sup35 protein. Science 277, 381–383.

Paushkin S. V., Kushnirov, V. V., Smirnov, V. N. and Ter-Avanesyan, M. D. (1997b). Interaction between yeast Sup45p(eRF1) and Sup35p(eRF3) polypeptide chain release factors: Implications for prion-dependent regulation. Mol. Cell. Biol. 17, 2798–2805.

Perlick, H. A., Medghalchi, S. M., Spencer, F. A., Kendzior, R. J. Jr. and Dietz, H. C. (1996) Mamnalian orthologues of a yeast regulator of nonsense-transcript stability. Proc. Natl. Acad. Sci. USA 93, 10928–10932.

Rose, M. D., Winston, D. F. and Hieter, P. (1990) Methods in Yeast Genetics. Cold Spring harbor Laboratory Press, Cold Spring Harbor, N.Y.

Rozen F, Edery I, Meerovitch K, Dever TE, Merrick WC, Sonenberg N. 1990. Bidirectional RNA helicase activity of eucaryotic translation intitiation factors 4A and 4F. *Mol Cell Biol* 10:1134–1144.

Ruiz-Echevarria, M. J., K. Czaplinski, and S. W. Peltz. (1996) Making sense of nonsense in yeast. *TIBS* 21, 433–438.

Ruiz-Echevarria, M. J., and Peltz, S. W. (1996). Utilizing the GCN4 leader region to investigate the role of the sequence determinants in nonsense-mediated mRNA decay. *EMBO J.* 15, 2810–2819.

Scheisti, R. H. and Geitz, R. D. (1989) High efficiency transformation of intact yeast cells using single stranded nucleic acids as a carrier. *Curr. Genetics* 16: 339–346.

Singh,A., Ursic,D. and Davies,J. 1979. Phenotypic suppression and misreading *Saccharomyces cerevisiae. Nature.* 277, 146–148.

Stansfield, I., Grant, C. M.,Akhmaloka, and Tuite, M. F. (1992) Ribosomal association of the yeast SAL4(SUP45) gene product: implications for its role in translation fidelity and termination. *Mol. Microbiol.* 6, 3469–3478.

Song J. M. and Liebman S. W. 1987. Allosuppressors that enhance the efficiency of omnipotent suppressors in *Saccharomyces cerevisiae Genetics* 115:451–460.

Stansfield, I., Jones, K. M., Kushnirov, V. V., Dagakesamanskaya, A. R., Poznyakov, A. I., Paushkin, S. V., Nierras, C. R., Cox, B. S., Ter-Avanesyan, M. D. and Tuite, M. F. (1995) The products of the SUP45(eRF1) and SUP35 genes interact to mediate translation termination in *Saccharomyces cerevisiae. EMBO J.* 14, 4365–4373.

Subramanya, H. S., Bird, L. E., Brannigan, J. A. and Wigley, D. B. 1996. Crystal structure of Dexx box DNA helicases. *Nature.* 384:379–383.

Venkatesan M, Silver LL, Nossal NG. 1982. Bacetriophage T4 Gene 41 protein, required for synthesis of RNA primers, is also a DNA helicase. *J Biol Chem* 257:12426–12434.

Weng, Y., Czaplinski, K. and Peltz, S. W. (1996a) Genetic and biochemical characterization of the mutations in the ATPase and helicase regions of Upf1Protein. *Mol. Cell. Biol.* 16, 5477–5490.

Weng, Y., Czaplinski, K. and Peltz, S. W. (1996b) Identification and characterization of mutations in the UPF1 gene that affect nonsense suppression and the formation of the Upf protein complex, but not mRNA turnover. *Mol. Cell. Biol.* 16, 5491–5506.

Weng, Y., Czaplinski, K. and Peltz, S. W. (1998) ATP is a cofactor of the Upf1protein that modulates it translation termination and RNA binding activities. *RNA* 4, 205–214.

Weng, Y., Ruiz-Echevarria, M. J., Zhang, S., Cui, Y., Czaplinski, K., Dinman J. D. and Peltz, S. W. (1997) Characterization of the nonsense-mediated mRNA decay pathway and its effect on modulating translation termination and programmed frameshifling. In: *mRNA Metabolism and Post-transcriptional Gene Regulation.* Modem Cell Biology 17, 241–263.

Winey, M. and M. R. Culbertson. 1988. Mutations affecting the tRNA-splicing endonuclease activity of *Saccharomyces cerevisiae. Genetics* 118:607–617.

Zhouravleva, G, Frolova, L., LeGoff, X., LeGuellec, R., Inge-Vechtomov, S., Kisselev, L. and Phillippe, M. (1995) Termination of translation in eukaryotes is governed by two interacting polypeptide chain release factors, eRF1 and eRF3. *EMBO J.* 14, 4065–4072.

What is claimed is:

1. A method of identifying a test composition or agent which increases nonsense suppression, comprising the steps of:
    (a) contacting Modulator of Translation Termination (Mtt1, also referred to as helicase B) in *S. cerevisiae* under conditions permitting binding between Mtt1 and the test composition or agent;
    (b) detecting specific binding of the test composition or agent to Mtt1; and
    (c) determining whether the test composition or agent increases nonsense suppression.

2. A method of identifying a test composition or agent which inhibits binding of Mtt1 (helicase B) to Eukaryotic Release Factor 3 (eRF3) in *S. cerevisiae*, comprising the steps of:
    (a) incubating components comprising the test composition or agent and Mtt1 (helicase B) wherein the incubating is carried out under conditions sufficient to permit the components to interact; and
    (b) contacting the test composition or agent with eRF3; and
    (c) determining whether the test composition or agent inhibits the binding of Mtt1 (helicase B) to eRF3.

3. A method of identifying a composition or agent which increases nonsense suppression by inhibiting the association of *S. cerevisiae* Mtt1 (helicase B) with ribosomes comprising the steps of:
    (a) introducing a test composition or agents into *S. cerevisiae* cells containing Mtt1 (helicase B);
    (b) determining whether the test composition or agent increases nonsense suppression; and
    (c) ascertaining the presence of Mtt1 (helicase B) in the polysome fraction.

4. A method of determining whether a test composition or agent increases nonsense suppression by inhibiting Mtt1 (helicase B)-mediated efficiency of translation termination, comprising the steps of:
    (a) providing an *S. cerevisiae* cell or *S. cerevisiae* cell extract comprising Mtt1 (helicase B) and one or more genes containing at least one premature stop codon;
    (b) contacting said cell or cell extract with the test composition or agent; and
    (c) detecting readthrough of at least one premature stop codon, wherein readthrough of the premature stop codon is indicative that the test composition or agent inhibits Mtt1 (helicase B)-mediated efficiency of translation termination.

* * * * *

SEQUENCE LISTING

```
<160> NUMBER OF SEQ ID NOS: 32

<210> SEQ ID NO 1
<211> LENGTH: 9
<212> TYPE: PRT
<213> ORGANISM: Saccharomyces cerevisiae
<220> FEATURE:
<223> OTHER INFORMATION: Xaa = any amino acid

<400> SEQUENCE: 1

Gly Pro Pro Gly Thr Lys Thr Xaa Thr
 1               5

<210> SEQ ID NO 2
<211> LENGTH: 14
<212> TYPE: PRT
<213> ORGANISM: Saccharomyces cerevisiae
<220> FEATURE:
<223> OTHER INFORMATION: Xaa = any amino acid

<400> SEQUENCE: 2

Arg Ile Leu Xaa Cys Ala Ser Asn Xaa Ala Val Asp Xaa Leu
 1               5                  10

<210> SEQ ID NO 3
<211> LENGTH: 17
<212> TYPE: PRT
<213> ORGANISM: Saccharomyces cerevisiae
<220> FEATURE:
<223> OTHER INFORMATION: Xaa = any amino acid
```

-continued

```
<400> SEQUENCE: 3

Val Val Ile Asp Glu Xaa Xaa Gln Ala Xaa Xaa Xaa Xaa Xaa Ile Pro
  1               5                  10                  15
Ile

<210> SEQ ID NO 4
<211> LENGTH: 12
<212> TYPE: PRT
<213> ORGANISM: Saccharomyces cerevisiae
<220> FEATURE:
<223> OTHER INFORMATION: Xaa = any amino acid

<400> SEQUENCE: 4

Xaa Xaa Ile Leu Ala Gly Asp Xaa Xaa Gln Leu Pro
  1               5                  10

<210> SEQ ID NO 5
<211> LENGTH: 9
<212> TYPE: PRT
<213> ORGANISM: Saccharomyces cerevisiae
<220> FEATURE:
<223> OTHER INFORMATION: Xaa= any amino acid

<400> SEQUENCE: 5

Leu Xaa Xaa Ser Leu Phe Glu Arg Val
  1               5

<210> SEQ ID NO 6
<211> LENGTH: 21
<212> TYPE: PRT
<213> ORGANISM: Saccharomyces cerevisiae
<220> FEATURE:
<223> OTHER INFORMATION: Xaa = any amino acid

<400> SEQUENCE: 6

Leu Xaa Xaa Gln Tyr Arg Met His Pro Xaa Ile Ser Glu Phe Pro Xaa
  1               5                  10                  15
Tyr Xaa Gly Xaa Leu
              20

<210> SEQ ID NO 7
<211> LENGTH: 14
<212> TYPE: PRT
<213> ORGANISM: saccharomyces cerevisiae
<220> FEATURE:
<223> OTHER INFORMATION: Xaa = any amino acid

<400> SEQUENCE: 7

Ile Gly Val Ile Thr Pro Tyr Xaa Xaa Gln Val Xaa Xaa Leu
  1               5                  10

<210> SEQ ID NO 8
<211> LENGTH: 23
<212> TYPE: PRT
<213> ORGANISM: Saccharomyces cerevisiae
<220> FEATURE:
<223> OTHER INFORMATION: Xaa = any amino acid

<400> SEQUENCE: 8

Val Glu Val Xaa Thr Val Asp Xaa Phe Gln Gly Arg Glu Lys Asp Xaa
  1               5                  10                  15
Ile Ile Leu Ser Cys Val Arg
              20
```

```
<210> SEQ ID NO 9
<211> LENGTH: 18
<212> TYPE: PRT
<213> ORGANISM: saccharomyces cerevisiae
<220> FEATURE:
<223> OTHER INFORMATION: Xaa = any amino acid

<400> SEQUENCE: 9

Ile Gly Phe Leu Xaa Asp Xaa Arg Arg Ile Asn Val Ala Leu Thr Arg
 1               5                  10                  15

Ala Lys

<210> SEQ ID NO 10
<211> LENGTH: 10
<212> TYPE: PRT
<213> ORGANISM: saccharomyces cerevisiae
<220> FEATURE:
<223> OTHER INFORMATION: Xaa = any amino acid

<400> SEQUENCE: 10

Leu Glu Xaa Ser Leu Phe Glu Arg Val Leu
 1               5                  10

<210> SEQ ID NO 11
<211> LENGTH: 10
<212> TYPE: PRT
<213> ORGANISM: saccharomyces cerevisiae
<220> FEATURE:
<223> OTHER INFORMATION: Xaa = any amino acid

<400> SEQUENCE: 11

Ile Gly Val Ile Thr Pro Tyr Xaa Ala Gln
 1               5                  10

<210> SEQ ID NO 12
<211> LENGTH: 11
<212> TYPE: PRT
<213> ORGANISM: saccharomyces cerevisisae

<400> SEQUENCE: 12

Leu Ile Gln Gly Pro Pro Gly Thr Gly Lys Thr
 1               5                  10

<210> SEQ ID NO 13
<211> LENGTH: 13
<212> TYPE: PRT
<213> ORGANISM: saccharomyces cerevisiae

<400> SEQUENCE: 13

Arg Ile Leu Val Cys Ala Pro Ser Asn Ile Ala Val Asp
 1               5                  10

<210> SEQ ID NO 14
<211> LENGTH: 5
<212> TYPE: PRT
<213> ORGANISM: saccharomyces cerevisiae

<400> SEQUENCE: 14

Ile Lys Ile Leu Arg
 1               5

<210> SEQ ID NO 15
<211> LENGTH: 4
<212> TYPE: PRT
<213> ORGANISM: saccharomyces cerevisiae
```

```
<400> SEQUENCE: 15

Lys Lys Arg Glu
  1

<210> SEQ ID NO 16
<211> LENGTH: 11
<212> TYPE: PRT
<213> ORGANISM: saccharomyces cerevisiae

<400> SEQUENCE: 16

Phe Asp Thr Val Ile Ile Asp Glu Ala Thr Gln
  1               5                  10

<210> SEQ ID NO 17
<211> LENGTH: 4
<212> TYPE: PRT
<213> ORGANISM: saccharomyces cerevisiae

<400> SEQUENCE: 17

Leu Ile Pro Leu
  1

<210> SEQ ID NO 18
<211> LENGTH: 5
<212> TYPE: PRT
<213> ORGANISM: saccharomyces cerevisiae

<400> SEQUENCE: 18

Ile Leu Val Gly Asp
  1               5

<210> SEQ ID NO 19
<211> LENGTH: 7
<212> TYPE: PRT
<213> ORGANISM: saccharomyces cerevisiae

<400> SEQUENCE: 19

Ser Leu Phe Glu Arg Val Leu
  1               5

<210> SEQ ID NO 20
<211> LENGTH: 6
<212> TYPE: PRT
<213> ORGANISM: saccharomyces cerevisiae

<400> SEQUENCE: 20

Gly Val Ile Thr Pro Tyr
  1               5

<210> SEQ ID NO 21
<211> LENGTH: 11
<212> TYPE: PRT
<213> ORGANISM: saccharomyces cerevisiae

<400> SEQUENCE: 21

Thr Val Asp Ala Phe Gln Gly Arg Glu Lys Asp
  1               5                  10

<210> SEQ ID NO 22
<211> LENGTH: 7
<212> TYPE: PRT
<213> ORGANISM: saccharomyces cerevisiae

<400> SEQUENCE: 22
```

```
Ile Ile Leu Ser Cys Val Arg
  1               5
```

<210> SEQ ID NO 23
<211> LENGTH: 6
<212> TYPE: PRT
<213> ORGANISM: saccharomyces cerevisiae

<400> SEQUENCE: 23

```
Ile Gly Phe Leu Lys Asp
  1               5
```

<210> SEQ ID NO 24
<211> LENGTH: 11
<212> TYPE: PRT
<213> ORGANISM: saccharomyces cerevisiae

<400> SEQUENCE: 24

```
Arg Arg Leu Asn Val Ala Leu Thr Arg Ala Lys
  1               5                  10
```

<210> SEQ ID NO 25
<211> LENGTH: 415
<212> TYPE: PRT
<213> ORGANISM: saccharomyces cerevisiae

<400> SEQUENCE: 25

```
Leu Gln Gly Pro Pro Gly Thr Gly Lys Thr Ser Thr Ile Glu Glu Ile
  1               5                  10                  15

Ile Ile Gln Val Ile Glu Arg Phe His Ala Phe Pro Ile Leu Cys Val
             20                  25                  30

Ala Ala Ser Asn Ile Ala Ile Asp Asn Ile Ala Glu Lys Ile Met Glu
         35                  40                  45

Asn Arg Pro Gln Ile Lys Ile Leu Arg Ile Leu Ser Lys Lys Lys Glu
     50                  55                  60

Gln Gln Tyr Ser Asp Asp His Pro Leu Gly Glu Ile Cys Leu His Asn
 65                  70                  75                  80

Ile Val Tyr Lys Asn Leu Ser Pro Asp Met Gln Val Val Ala Asn Lys
                 85                  90                  95

Thr Arg Arg Gly Glu Met Ile Ser Lys Ser Glu Asp Thr Lys Phe Tyr
            100                 105                 110

Lys Glu Lys Asn Arg Val Thr Asn Lys Val Val Ser Gln Ser Gln Ile
        115                 120                 125

Ile Phe Thr Thr Asn Ile Ala Ala Gly Gly Arg Glu Leu Lys Val Ile
    130                 135                 140

Lys Glu Cys Pro Val Val Ile Met Asp Glu Ala Thr Gln Ser Ser Glu
145                 150                 155                 160

Ala Ser Thr Leu Val Pro Leu Ser Leu Pro Gly Ile Arg Asn Phe Val
                165                 170                 175

Phe Val Gly Asp Glu Lys Gln Leu Ser Ser Phe Ser Asn Ile Pro Gln
            180                 185                 190

Leu Glu Thr Ser Leu Phe Glu Arg Val Leu Ser Asn Gly Thr Tyr Lys
        195                 200                 205

Asn Pro Leu Met Leu Asp Thr Gln Tyr Arg Met His Pro Lys Ile Ser
    210                 215                 220

Glu Phe Pro Ile Lys Ile Tyr Asn Gly Glu Leu Lys Asp Gly Val
225                 230                 235                 240
```

-continued

Thr Asp Glu Gln Lys Ala Trp Pro Gly Val Gln His Pro Leu Phe Phe
             245                 250                 255

Tyr Gln Cys Asp Leu Gly Pro Glu Ser Arg Val Arg Ser Thr Gln Arg
         260                 265                 270

Asp Ile Val Gly Phe Thr Tyr Glu Asn Lys His Glu Cys Val Glu Ile
         275                 280                 285

Val Lys Ile Ile Gln Ile Leu Met Leu Asp Lys Lys Val Pro Leu Glu
    290                 295                 300

Glu Ile Gly Val Ile Thr Pro Tyr Ser Ala Gln Arg Asp Leu Leu Ser
305                 310                 315                 320

Asp Ile Leu Thr Lys Asn Val Val Ile Asn Pro Lys Gln Ile Ser Met
             325                 330                 335

Gln Gln Glu Tyr Asp Glu Ile Glu Leu Phe Asn Ala Ala Gly Ser Gln
             340                 345                 350

Gly Thr Ala Gly Ser Leu Gln Asn Asn Val Ile Asn Ile Ile Asn Gly
             355                 360                 365

Leu His Val Ala Thr Val Asp Ser Phe Gln Gly His Glu Lys Ser Phe
         370                 375                 380

Ile Ile Phe Ser Cys Val Arg Asn Asn Thr Glu Asn Lys Ile Gly Phe
385                 390                 395                 400

Leu Arg Asp Lys Arg Arg Leu Asn Val Ala Leu Thr Arg Ala Lys
                 405                 410                 415

<210> SEQ ID NO 26
<211> LENGTH: 472
<212> TYPE: PRT
<213> ORGANISM: saccharomyces cerevisiae

<400> SEQUENCE: 26

Phe Leu Ser Leu Ile Gln Gly Pro Gly Thr Gly Lys Thr Lys Thr
1               5                   10                  15

Ile Leu Gly Ile Ile Gly Tyr Phe Leu Ser Thr Lys Asn Ala Ser Ser
             20                  25                  30

Ser Asn Val Ile Lys Val Pro Leu Glu Lys Asn Ser Ser Asn Thr Glu
         35                  40                  45

Gln Leu Leu Lys Lys Gln Lys Ile Leu Ile Cys Ala Pro Ser Asn Ala
    50                  55                  60

Ala Val Asp Glu Ile Cys Leu Arg Leu Lys Ser Gly Val Tyr Asp Lys
65                  70                  75                  80

Gln Gly His Gln Phe Lys Pro Gln Leu Val Arg Val Gly Arg Ser Asp
             85                  90                  95

Val Val Asn Val Ala Ile Lys Asp Leu Thr Leu Glu Glu Leu Val Asp
         100                 105                 110

Lys Arg Ile Gly Glu Arg Asn Tyr Glu Ile Arg Thr Asp Pro Glu Leu
    115                 120                 125

Glu Arg Lys Phe Asn Asn Ala Val Thr Lys Arg Arg Glu Leu Arg Gly
130                 135                 140

Lys Leu Asp Ser Glu Ser Gly Asn Pro Glu Pro Met Ser Thr Glu
145                 150                 155             160

Asp Ile Ser Lys Leu Gln Leu Lys Ile Arg Glu Leu Ser Lys Ile Ile
             165                 170                 175

Asn Glu Leu Gly Arg Asp Arg Asp Glu Met Arg Glu Lys Asn Ser Val
         180                 185                 190

Asn Tyr Arg Asn Arg Asp Leu Asp Arg Arg Asn Ala Gln Ala His Ile
    195                 200                 205

Leu Ala Val Ser Asp Ile Ile Cys Ser Thr Leu Ser Gly Ser Ala His
            210                 215                 220

Asp Val Leu Ala Thr Met Gly Ile Lys Phe Asp Thr Val Ile Ile Asp
225                 230                 235                 240

Glu Ala Cys Gln Cys Thr Glu Leu Ser Ser Ile Ile Pro Leu Arg Tyr
                245                 250                 255

Gly Gly Lys Arg Cys Ile Met Val Gly Asp Pro Asn Gln Leu Pro Pro
            260                 265                 270

Thr Val Leu Ser Gly Ala Ala Ser Asn Phe Lys Tyr Asn Gln Ser Leu
            275                 280                 285

Phe Val Arg Met Glu Lys Asn Ser Ser Pro Tyr Leu Leu Asp Val Gln
290                 295                 300

Tyr Arg Met His Pro Ser Ile Ser Lys Phe Pro Ser Ser Glu Phe Tyr
305                 310                 315                 320

Gln Gly Arg Leu Lys Asp Gly Pro Gly Met Asp Ile Leu Asn Lys Arg
                325                 330                 335

Pro Trp His Gln Leu Glu Pro Leu Ala Pro Tyr Lys Phe Phe Asp Ile
            340                 345                 350

Ile Ser Gly Arg Gln Glu Gln Asn Ala Lys Thr Met Ser Tyr Thr Asn
            355                 360                 365

Met Glu Glu Ile Arg Val Ala Ile Glu Leu Val Asp Tyr Leu Phe Arg
370                 375                 380

Lys Phe Asp Asn Lys Ile Asp Phe Thr Gly Lys Ile Gly Ile Ile Ser
385                 390                 395                 400

Pro Tyr Arg Glu Gln Met Gln Lys Met Arg Lys Glu Phe Ala Arg Tyr
                405                 410                 415

Phe Gly Gly Met Ile Asn Lys Ser Ile Asp Phe Asn Thr Ile Asp Gly
            420                 425                 430

Phe Gln Gly Gln Glu Lys Glu Ile Ile Leu Ile Ser Cys Val Arg Ala
            435                 440                 445

Asp Asp Thr Lys Ser Ser Val Gly Phe Leu Lys Asp Phe Arg Arg Met
    450                 455                 460

Asn Val Ala Leu Thr Arg Ala Lys
465                 470

<210> SEQ ID NO 27
<211> LENGTH: 366
<212> TYPE: PRT
<213> ORGANISM: saccharomyces cerevisiae

<400> SEQUENCE: 27

Tyr Ala Leu Ile Leu Gly Met Pro Gly Thr Gly Lys Thr Thr Val Ile
  1               5                  10                  15

Ala Glu Ile Ile Lys Ile Leu Val Ser Glu Gly Lys Arg Val Leu Leu
                20                  25                  30

Thr Ser Tyr Thr His Ser Ala Val Asp Asn Ile Leu Ile Lys Leu Arg
            35                  40                  45

Asn Thr Asn Ile Ser Ile Met Arg Leu Gly Met Lys His Lys Val His
        50                  55                  60

Pro Asp Thr Gln Lys Tyr Val Pro Asn Tyr Ala Ser Val Lys Ser Tyr
65                  70                  75                  80

Asn Asp Tyr Leu Ser Lys Ile Asn Ser Thr Ser Val Val Ala Thr Thr
                85                  90                  95

Cys Leu Gly Ile Asn Asp Ile Leu Phe Thr Leu Asn Glu Lys Asp Phe

```
            100                 105                 110
Asp Tyr Val Ile Leu Asp Glu Ala Ser Gln Ile Ser Met Pro Val Ala
            115                 120                 125
Leu Gly Pro Leu Arg Tyr Gly Asn Arg Phe Ile Met Val Gly Asp His
            130                 135                 140
Tyr Gln Leu Pro Pro Leu Val Lys Asn Asp Ala Ala Arg Leu Gly Gly
145                 150                 155                 160
Leu Glu Glu Ser Leu Phe Lys Thr Phe Cys Glu Lys His Pro Glu Ser
            165                 170                 175
Val Ala Glu Leu Thr Leu Gln Tyr Arg Met Cys Gly Asp Ile Val Thr
            180                 185                 190
Leu Ser Asn Phe Leu Ile Tyr Asp Asn Lys Leu Lys Cys Gly Asn Asn
            195                 200                 205
Glu Val Phe Ala Gln Ser Leu Glu Leu Pro Met Pro Glu Ala Leu Ser
            210                 215                 220
Arg Tyr Arg Asn Glu Ser Ala Asn Ser Lys Gln Trp Leu Glu Asp Ile
225                 230                 235                 240
Leu Glu Pro Thr Arg Lys Val Val Phe Leu Asn Tyr Asp Asn Cys Pro
            245                 250                 255
Asp Ile Ile Glu Gln Ser Glu Lys Asp Asn Ile Thr Asn His Gly Glu
            260                 265                 270
Ala Glu Leu Thr Leu Gln Cys Val Glu Gly Met Leu Leu Ser Gly Val
            275                 280                 285
Pro Cys Glu Asp Ile Gly Val Met Thr Leu Tyr Arg Ala Gln Leu Arg
            290                 295                 300
Leu Leu Lys Lys Ile Phe Asn Lys Asn Val Tyr Asp Gly Leu Glu Ile
305                 310                 315                 320
Leu Thr Ala Asp Gln Phe Gln Gly Arg Asp Lys Lys Cys Ile Ile Ile
            325                 330                 335
Ser Met Val Arg Arg Asn Ser Gln Leu Asn Gly Gly Ala Leu Leu Lys
            340                 345                 350
Glu Leu Arg Arg Val Asn Val Ala Met Thr Arg Ala Lys Ser
            355                 360                 365

<210> SEQ ID NO 28
<211> LENGTH: 414
<212> TYPE: PRT
<213> ORGANISM: saccharomyces cerevisiae

<400> SEQUENCE: 28

His Gly Pro Pro Gly Thr Gly Lys Thr Phe Thr Leu Ile Glu Leu Ile
1               5                   10                  15
Gln Gln Leu Leu Ile Lys Asn Pro Glu Glu Arg Ile Leu Ile Cys Gly
            20                  25                  30
Pro Ser Asn Ile Ser Val Asp Thr Ile Leu Glu Arg Leu Thr Pro Leu
        35                  40                  45
Val Pro Asn Asn Leu Leu Leu Arg Ile Gly His Pro Ala Arg Leu Leu
    50                  55                  60
Asp Ser Asn Lys Arg His Ser Leu Asp Ile Leu Ser Lys Lys Asn Thr
65                  70                  75                  80
Ile Val Lys Asp Ile Ser Gln Glu Ile Asp Lys Leu Ile Gln Glu Asn
                85                  90                  95
Lys Lys Leu Lys Asn Tyr Lys Gln Arg Lys Glu Asn Trp Asn Glu Ile
            100                 105                 110
```

-continued

```
Lys Leu Leu Arg Lys Asp Leu Lys Arg Glu Phe Lys Thr Ile Lys
        115                 120                 125

Asp Leu Ile Ile Gln Ser Arg Ile Val Val Thr Thr Leu His Gly Ser
    130                 135                 140

Ser Ser Arg Glu Leu Cys Ser Leu Tyr Arg Asp Asp Pro Asn Phe Gln
145                 150                 155                 160

Leu Phe Asp Thr Leu Ile Ile Asp Glu Val Ser Gln Ala Met Glu Pro
                165                 170                 175

Gln Cys Trp Ile Pro Leu Ile Ala His Gln Asn Gln Phe His Lys Leu
            180                 185                 190

Val Leu Ala Gly Asp Asn Lys Gln Leu Pro Pro Thr Ile Lys Thr Glu
        195                 200                 205

Asp Asp Lys Asn Val Ile His Asn Leu Glu Thr Thr Leu Phe Asp Arg
    210                 215                 220

Ile Ile Lys Ile Phe Pro Lys Arg Asp Met Val Lys Phe Leu Asn Val
225                 230                 235                 240

Gln Tyr Arg Met Asn Gln Lys Ile Met Glu Phe Pro Ser His Ser Met
                245                 250                 255

Tyr Asn Gly Lys Leu Leu Ala Asp Ala Thr Val Ala Asn Arg Leu Leu
            260                 265                 270

Ile Asp Leu Pro Thr Val Asp Ala Thr Pro Ser Glu Asp Asp Asp
        275                 280                 285

Thr Lys Ile Pro Leu Ile Trp Tyr Asp Thr Gln Gly Asp Glu Phe Gln
    290                 295                 300

Glu Thr Ala Asp Glu Ala Thr Ile Leu Gly Ser Lys Tyr Asn Glu Gly
305                 310                 315                 320

Glu Ile Ala Ile Val Lys Glu His Ile Glu Asn Leu Arg Ser Phe Asn
                325                 330                 335

Val Pro Glu Asn Ser Ile Gly Val Ile Ser Pro Tyr Asn Ala Gln Val
            340                 345                 350

Ser His Leu Lys Lys Leu Ile His Asp Glu Leu Lys Leu Thr Asp Ile
        355                 360                 365

Glu Ile Ser Thr Val Asp Gly Phe Gln Gly Arg Glu Lys Asp Val Ile
    370                 375                 380

Ile Leu Ser Leu Val Arg Ser Asn Glu Lys Phe Glu Val Gly Phe Leu
385                 390                 395                 400

Lys Glu Glu Arg Arg Leu Asn Val Ala Met Thr Arg Pro Arg
                405                 410
```

<210> SEQ ID NO 29
<211> LENGTH: 380
<212> TYPE: PRT
<213> ORGANISM: saccharomyces cerevisiae

<400> SEQUENCE: 29

```
Pro Leu Ser Leu Ile Gln Gly Pro Pro Gly Thr Gly Lys Thr Val Thr
  1               5                  10                  15

Ser Ala Thr Ile Val Tyr His Leu Ser Lys Ile His Lys Asp Arg Ile
                20                  25                  30

Leu Val Cys Ala Pro Ser Asn Val Ala Val Asp His Leu Ala Ala Lys
            35                  40                  45

Leu Arg Asp Leu Gly Leu Lys Val Val Arg Leu Thr Ala Lys Ser Arg
        50                  55                  60

Glu Asp Val Glu Ser Ser Val Ser Asn Leu Ala Leu His Asn Leu Val
 65                  70                  75                  80
```

Gly Arg Gly Ala Lys Gly Glu Leu Lys Asn Leu Leu Lys Leu Lys Asp
                85                  90                  95

Glu Val Gly Glu Leu Ser Ala Asp Ser Thr Lys Arg Phe Val Lys Leu
            100                 105                 110

Val Arg Lys Thr Glu Ala Glu Ile Leu Asn Lys Ala Asp Val Val Cys
        115                 120                 125

Cys Thr Cys Val Gly Ala Gly Asp Lys Arg Leu Asp Thr Lys Phe Arg
    130                 135                 140

Thr Val Leu Ile Asp Glu Ser Thr Gln Ala Ser Glu Pro Glu Cys Leu
145                 150                 155                 160

Ile Pro Ile Val Lys Gly Ala Lys Gln Val Ile Leu Val Gly Asp His
                165                 170                 175

Gln Gln Leu Gly Pro Val Ile Leu Glu Arg Lys Ala Ala Asp Ala Gly
            180                 185                 190

Leu Lys Gln Ser Leu Phe Glu Arg Leu Ile Ser Leu Gly His Val Pro
        195                 200                 205

Ile Arg Leu Glu Val Gln Tyr Arg Met Asn Pro Tyr Leu Ser Glu Phe
    210                 215                 220

Pro Ser Asn Met Phe Tyr Glu Gly Ser Leu Gln Asn Gly Val Thr Ile
225                 230                 235                 240

Glu Gln Arg Thr Val Pro Asn Ser Lys Phe Pro Trp Pro Ile Arg Gly
                245                 250                 255

Ile Pro Met Met Phe Trp Ala Asn Tyr Gly Arg Glu Glu Ile Ser Ala
            260                 265                 270

Asn Gly Thr Ser Phe Leu Asn Arg Ile Glu Ala Met Asn Cys Glu Arg
        275                 280                 285

Ile Ile Thr Lys Leu Phe Arg Asp Gly Val Lys Pro Glu Gln Ile Gly
    290                 295                 300

Val Ile Thr Pro Tyr Glu Gly Gln Arg Ala Tyr Ile Leu Gln Tyr Met
305                 310                 315                 320

Gln Met Asn Gly Ser Leu Asp Lys Asp Leu Tyr Lys Ile Val Glu Val
                325                 330                 335

Ala Ser Val Asp Ala Phe Gln Gly Arg Glu Lys Asp Tyr Ile Ile Leu
            340                 345                 350

Ser Cys Val Arg Ala Asn Glu Gln Gln Ala Ile Gly Phe Leu Arg Asp
        355                 360                 365

Pro Arg Arg Leu Asn Val Gly Leu Thr Arg Ala Lys
    370                 375                 380

<210> SEQ ID NO 30
<211> LENGTH: 7
<212> TYPE: PRT
<213> ORGANISM: Saccharomyces cerevisiae

<400> SEQUENCE: 30

Leu Asp Val Gln Tyr Arg Met
 1               5

<210> SEQ ID NO 31
<211> LENGTH: 6
<212> TYPE: PRT
<213> ORGANISM: Saccharomyces cerevisiae

<400> SEQUENCE: 31

Ile Ser Glu Phe Pro Ser
 1               5

```
<210> SEQ ID NO 32
<211> LENGTH: 6
<212> TYPE: PRT
<213> ORGANISM: Saccharomyces cerevisiae

<400> SEQUENCE: 32

Ile Tyr Asn Gly Arg Leu
 1               5
```